(12) United States Patent
Zhou et al.

(10) Patent No.: US 10,821,140 B2
(45) Date of Patent: Nov. 3, 2020

(54) CONSTRUCTION OF ONCOLYTIC HERPES SIMPLEX VIRUSES (OHSV) OBLIGATE VECTOR AND CONSTRUCTS FOR CANCER THERAPY

(71) Applicant: IMMVIRA CO., LIMITED, Shenzhen (CN)

(72) Inventors: Grace Guoying Zhou, Guangzhou (CN); Xiaoqing Chen, Shenzhen (CN); Xianjie Liu, Shenzhen (CN)

(73) Assignee: IMMVIRA CO., LIMITED, Shenzhen (CN)

( * ) Notice: Subject to any disclaimer, the term of this patent is extended or adjusted under 35 U.S.C. 154(b) by 0 days.

(21) Appl. No.: 16/077,417

(22) PCT Filed: Apr. 22, 2016

(86) PCT No.: PCT/CN2016/080025
§ 371 (c)(1),
(2) Date: Aug. 10, 2018

(87) PCT Pub. No.: WO2017/181420
PCT Pub. Date: Oct. 26, 2017

(65) Prior Publication Data
US 2019/0083555 A1 Mar. 21, 2019

(51) Int. Cl.
| | | |
|---|---|---|
| *A61K 35/763* | (2015.01) | |
| *C07K 16/28* | (2006.01) | |
| *C12N 15/86* | (2006.01) | |
| *A61P 35/00* | (2006.01) | |
| *C07K 14/54* | (2006.01) | |

(52) U.S. Cl.
CPC ............ *A61K 35/763* (2013.01); *A61P 35/00* (2018.01); *C07K 14/5434* (2013.01); *C07K 16/2818* (2013.01); *C12N 15/86* (2013.01); *C07K 2317/622* (2013.01); *C12N 2710/16621* (2013.01); *C12N 2710/16632* (2013.01); *C12N 2710/16643* (2013.01)

(58) Field of Classification Search
CPC ...... A61K 35/763; A61K 35/76; A61K 48/00; C12N 15/86; C12N 2710/16621; C12N 2710/16632; C12N 2710/16643; A61P 35/00; C07K 14/5434; C07K 16/2818; C07K 2317/622
See application file for complete search history.

(56) References Cited

U.S. PATENT DOCUMENTS

| | | | | | |
|---|---|---|---|---|---|
| 5,837,532 | A | * | 11/1998 | Preston | C12N 7/00 435/320.1 |
| 5,851,826 | A | * | 12/1998 | Fraefel | C07K 14/005 435/325 |
| 6,248,320 | B1 | * | 6/2001 | Coffin | A61P 25/16 424/93.2 |
| 6,719,982 | B1 | * | 4/2004 | Coffin | C07K 14/005 424/231.1 |
| 2002/0028925 | A1 | * | 3/2002 | Preston | C12N 7/00 536/23.72 |
| 2003/0207829 | A9 | * | 11/2003 | Weichselbaum | C07K 14/005 514/44 R |
| 2004/0228876 | A1 | * | 11/2004 | Nishiyama | C12N 7/00 424/199.1 |
| 2009/0176203 | A1 | * | 7/2009 | Conner | C12N 15/86 435/5 |
| 2010/0040614 | A1 | * | 2/2010 | Ahmed | A61K 39/12 424/133.1 |

FOREIGN PATENT DOCUMENTS

| | | |
|---|---|---|
| CN | 101376892 | 3/2009 |
| CN | 103589754 | 2/2014 |
| WO | WO 2000/45853 | 8/2000 |
| WO | WO-2000/045853 | 8/2000 |
| WO | WO-2000/065078 | 11/2000 |
| WO | WO 2014/047350 | 3/2014 |
| WO | WO-2015/009952 | 1/2015 |
| WO | WO 2015/066042 | 5/2015 |
| WO | WO-2017083291 A1 * | 5/2017 ......... C07K 14/5434 |

OTHER PUBLICATIONS

Miyagawa Y, Marino P, Verlengia G, Uchida H, Goins WF, Yokota S, Geller DA, Yoshida O, Mester J, Cohen JB, Glorioso JC. Herpes simplex viral-vector design for efficient transduction of nonneuronal cells without cytotoxicity. Proc Natl Acad Sci U S A. Mar. 31, 2015;112(13):E1632-41. Epub Mar. 16, 2015.*
Khalique H. "Transcriptional Control of ICP0 and its Effects on Herpes Simplex Virus-1 Replication." Doctoral thesis. Lim, F, mentor. Madrid, Spain. Apr. 2015. https://repositorio.uam.es/bitstream/handle/10486/667411/khalique_hena.pdf?sequence=1.*
Jenkins FJ, Donoghue AM, Martin Jr. Deletion of the Herpes simplex 1 internal repeat sequences affects pathogenicity in the mouse. Front Biosci. Oct. 4, 1996;1:a59-68.*
Jenkins FJ, Martin Jr. Role of the herpes simplex virus 1 internal repeat sequences in pathogenicity. Intervirology. 1990;31(2-4): 129-38. PubMed PMID: 2165040.*
Shen Y, Nemunaitis J. Herpes simplex virus 1 (HSV-1) for cancer treatment. Cancer Gene Ther. Nov. 2006;13(11):975-92. Epub Apr. 7, 2006.*
Extended European Search Report for EP Application No. 16899007.5 dated Apr. 8, 2019 (7 pages).
Hui et al., "The research prograss on HSV-1 oncolytic virus", Chinese Bulletin of Life Sciences, vol. 24, No. 3, Mar. 2012, pp. 236-241.
Sokolowski et al., "Oncolytic virotherapy using herpes simplex virus: how far have we come?" Oncolytic Virotherapy, Apr. 2015, pp. 207-219.

(Continued)

*Primary Examiner* — Rachel B Gill
(74) *Attorney, Agent, or Firm* — Sheppard Mullin Richter & Hampton LLP

(57) ABSTRACT

An obligate oHSV vector comprising modified viral DNA genome is provided. A recombinant oHSV-1 construct comprising the obligate oHSV vector and a heterologous nucleic acid sequence encoding an immunostimulatory and/or immunotherapeutic agent is also provided. Compositions comprising the recombinant oHSV-1 construct can be used for treating cancers.

29 Claims, 6 Drawing Sheets
Specification includes a Sequence Listing.

(56) References Cited

OTHER PUBLICATIONS

Taiwan First Office Action for Taiwanese Patent Application No. 106136397 dated Feb. 12, 2019 (5 pages).

Cozzi et al., "Oncolytic Viral Gene Therapy for Prostate Cancer Using Two Attenuated, Replication-Competent, Genetically Engineered Herpes Simplex Viruses", Prostate, 2002, 53, p. 95-100.

Currier et al., "Widespread intratumoral virus distribution with fractionated injection enables local control of large human rhabdomyosarcoma xenografts by oncolytic herpes simplex viruses", Cancer Gene Therapy, 2005, 12, p. 407-416.

International Search Report and Written Opinion for International Application No. PCT/CN2016/080025 dated Jan. 4, 2017. (9 pages).

Passer et al., "Combination of vinblastine and oncolytic herpes simplex virus vector expressing IL-12 therapy increases antitumor and antiangiogenic effects in prostate cancer models", Cancer Gene Therapy, 2013, 20, p. 17-24.

Takaoka et al., "A novel fusogenic herpes simplex virus for oncolytic virotherapy of squamous cell carcinoma", Virology Journal, 2011, 8:294, p. 1-12.

* cited by examiner

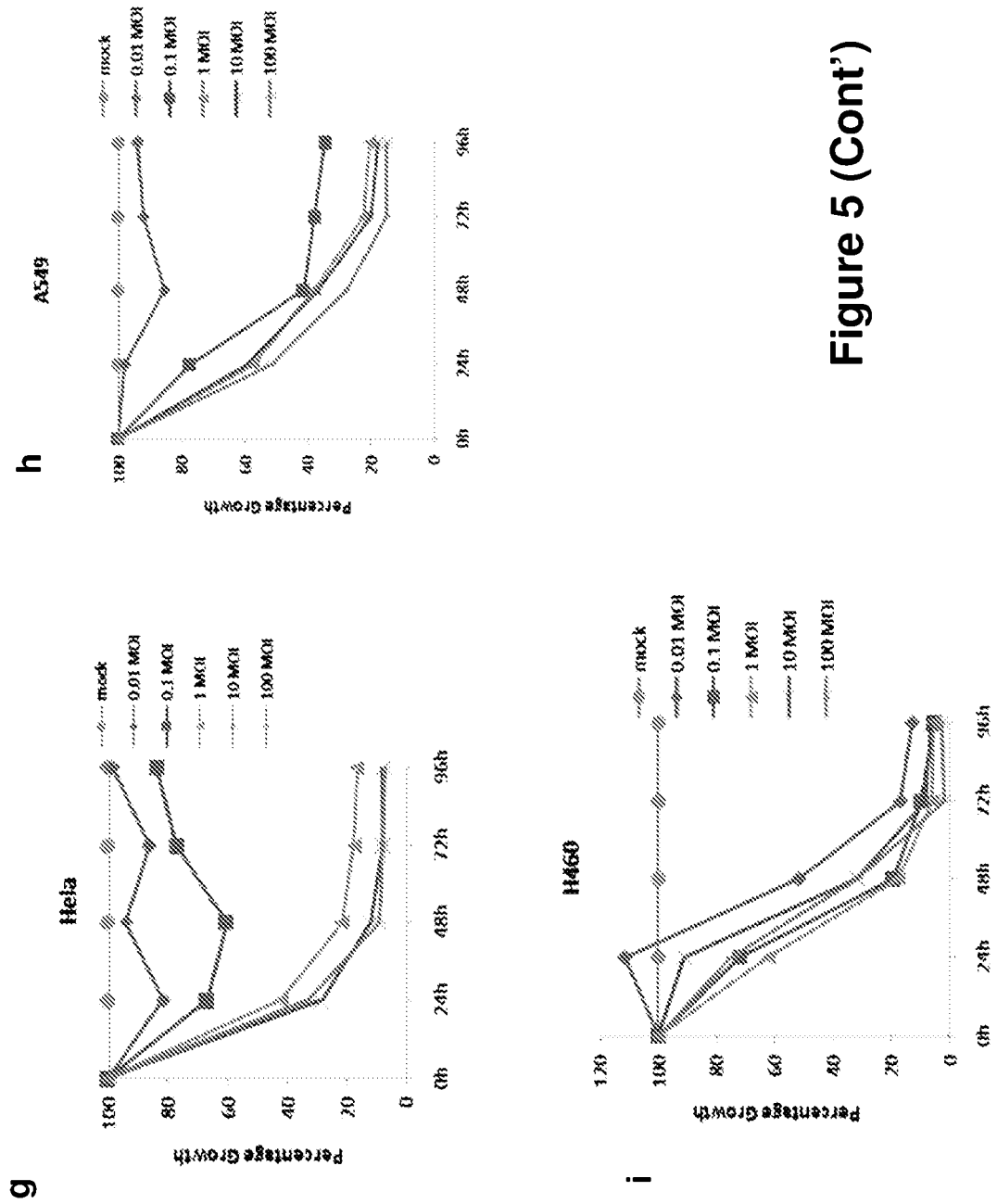
Figure 5 (Cont')

SEQUENCE LISTING

<160> NUMBER OF SEQ ID NOS: 9

<210> SEQ ID NO 1
<211> LENGTH: 798
<212> TYPE: DNA
<213> ORGANISM: Mouse

<400> SEQUENCE: 1

| | | | | | |
|---|---|---|---|---|---|
| atgggatggt | catgtatcat | ccttttcta | gtagcaactg | caaccggcgc | gcactccgag | 60 |
| gtgcagctgg | tgcagtctgg | gggaggcgtg | gttcagcctg | gaggtccct | gagactctcc | 120 |
| tgtgcagcgt | ctggattcac | ctttagtagc | tattggatga | gctgggtccg | ccaggctcca | 180 |
| gggaagggc | tggagtgggt | ctcagctatt | agtggtagtg | gtggtagcac | atactacgca | 240 |
| gactccgtga | agggccggtt | caccatctcc | agagacaatt | ccaagaacac | gctgtatctg | 300 |
| caaatgaaca | gcctaagagc | cgaggacacg | gccgtatatt | actgtgcgaa | agagaactgg | 360 |
| ggatcgtact | tcgatctctg | ggggcaaggg | accacggtca | ccgtctcctc | aggtggcgga | 420 |
| gggtcaggtg | gcggagggtc | aggtggcgga | gggtcaggcg | tgcactccga | catcgtgatg | 480 |
| acccagtctc | cttccaccct | gtctgcatct | gtaggagaca | gagtcaccat | cacttgccgg | 540 |
| gccagtcagg | gtattagtag | ctggttggcc | tggtatcagc | agaaaccagg | gagagcccct | 600 |
| aaggtcttga | tctataaggc | atcactttta | gaaagtgggg | tcccatcaag | gttcagcggc | 660 |
| agtggatctg | gacagatttc | actctcacc | atcagcagtc | tgcaacctga | agattttgca | 720 |
| acttactact | gtcaacagag | ttacagtacc | ccgtggacgt | tcggccaggg | gaccaagctg | 780 |
| gaaatcaaga | gatgataa | | | | | 798 |

<210> SEQ ID NO 2
<211> LENGTH: 264
<212> TYPE: PRT
<213> ORGANISM: Mouse

<400> SEQUENCE: 2

Met Gly Trp Ser Cys Ile Ile Leu Phe Leu Val Ala Thr Ala Thr Gly
1               5                   10                  15

Ala His Ser Glu Val Gln Leu Val Gln Ser Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Trp Met Ser Trp Val Arg Gln Ala Pro Gly Lys Gly Leu
    50                  55                  60

Glu Trp Val Ser Ala Ile Ser Gly Ser Gly Gly Ser Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Glu Asn Trp Gly Ser Tyr Phe Asp Leu Trp Gly
        115                 120                 125

Gln Gly Thr Thr Val Thr Val Ser Ser Gly Gly Gly Ser Gly Gly
    130                 135                 140

Gly Gly Ser Gly Gly Gly Gly Ser Gly Val His Ser Asp Ile Val Met
145                 150                 155                 160

Thr Gln Ser Pro Ser Thr Leu Ser Ala Ser Val Gly Asp Arg Val Thr
                165                 170                 175

```
Ile Thr Cys Arg Ala Ser Gln Gly Ile Ser Ser Trp Leu Ala Trp Tyr
            180                 185                 190

Gln Gln Lys Pro Gly Arg Ala Pro Lys Val Leu Ile Tyr Lys Ala Ser
        195                 200                 205

Thr Leu Glu Ser Gly Val Pro Ser Arg Phe Ser Gly Ser Gly Ser Gly
    210                 215                 220

Thr Asp Phe Thr Leu Thr Ile Ser Ser Leu Gln Pro Glu Asp Phe Ala
225                 230                 235                 240

Thr Tyr Tyr Cys Gln Gln Ser Tyr Ser Thr Pro Trp Thr Phe Gly Gln
                245                 250                 255

Gly Thr Lys Leu Glu Ile Lys Arg
            260
```

```
<210> SEQ ID NO 3
<211> LENGTH: 21
<212> TYPE: DNA
<213> ORGANISM: Artificial Sequence
<220> FEATURE:
<223> OTHER INFORMATION: Cassettes of CMV promoter producing 3 STOP
      codons

<400> SEQUENCE: 3
atgcaggtgc agtaatagta a                                             21

<210> SEQ ID NO 4
<211> LENGTH: 31
<212> TYPE: DNA
<213> ORGANISM: Artificial Sequence
<220> FEATURE:
<223> OTHER INFORMATION: A primer for amplifying the gene cassette
      flanked by upstream of nucleotides 117005 and downstream of
      nucleotides 132096 in the context of a wild type genome.

<400> SEQUENCE: 4
gaagatctaa tatttttatt gcaactccct g                                  31

<210> SEQ ID NO 5
<211> LENGTH: 783
<212> TYPE: DNA
<213> ORGANISM: Mouse

<400> SEQUENCE: 5
atgggatggt catgtatcat ccttttttcta gtagcaactg caacccagat ccagcttcag    60
gagtcaggac ctggcctggt gaacccctca caatcactgt ccctctcttg ctctgtcact   120
ggttactcca tcaccagtgg ttatggatgg aactggatca ggcagttccc agggcagaag   180
gtggagtgga tgggattcat atattatgag ggtagcacct actacaaccc ttccatcaag   240
agccgcatct ccatcaccag agacacatcg aagaaccagt tcttcctgca ggtgaattct   300
gtgaccactg aggacacagc cacatattac tgtgcgagac aaactgggta ctttgattac   360
tggggccaag gaaccatggt caccgtctcc tcaggtggtg gtggatcagg tggaggcgga   420
agtggaggtg gcggttccga catcatgatg acccagtctc cttcatccct gagtgtgtca   480
gcggagagaa agccactat cagctgcaag tccagtcaga gtcttttcaa cagtaacgcc   540
aaaacgaact acttgaactg gtatttgcag aaaccagggc agtctcctaa actgctgatc   600
tattatgcat ccactaggca tactggggtc cctgatcgct tcagaggcag tggatctggg   660
acggatttca ctctcaccat cagcagtgtc caggatgaag acctggcatt ttattactgt   720
cagcagtggt atgactaccc atacacgttc ggagctggga ccaaggtgga aatcaaatga   780
```

-continued

```
taa                                                                    783

<210> SEQ ID NO 6
<211> LENGTH: 259
<212> TYPE: PRT
<213> ORGANISM: Mouse

<400> SEQUENCE: 6

Met Gly Trp Ser Cys Ile Ile Leu Phe Leu Val Ala Thr Ala Thr Gln
1               5                   10                  15

Ile Gln Leu Gln Glu Ser Gly Pro Gly Leu Val Asn Pro Ser Gln Ser
            20                  25                  30

Leu Ser Leu Ser Cys Ser Val Thr Gly Tyr Ser Ile Thr Ser Gly Tyr
        35                  40                  45

Gly Trp Asn Trp Ile Arg Gln Phe Pro Gly Gln Lys Val Glu Trp Met
50                  55                  60

Gly Phe Ile Tyr Tyr Glu Gly Ser Thr Tyr Tyr Asn Pro Ser Ile Lys
65                  70                  75                  80

Ser Arg Ile Ser Ile Thr Arg Asp Thr Ser Lys Asn Gln Phe Phe Leu
                85                  90                  95

Gln Val Asn Ser Val Thr Thr Glu Asp Thr Ala Thr Tyr Tyr Cys Ala
            100                 105                 110

Arg Gln Thr Gly Tyr Phe Asp Tyr Trp Gly Gln Gly Thr Met Val Thr
        115                 120                 125

Val Ser Ser Gly Gly Gly Gly Ser Gly Gly Gly Gly Ser Gly Gly Gly
130                 135                 140

Gly Ser Asp Ile Met Met Thr Gln Ser Pro Ser Ser Leu Ser Val Ser
145                 150                 155                 160

Ala Gly Glu Lys Ala Thr Ile Ser Cys Lys Ser Ser Gln Ser Leu Phe
                165                 170                 175

Asn Ser Asn Ala Lys Thr Asn Tyr Leu Asn Trp Tyr Leu Gln Lys Pro
            180                 185                 190

Gly Gln Ser Pro Lys Leu Leu Ile Tyr Tyr Ala Ser Thr Arg His Thr
        195                 200                 205

Gly Val Pro Asp Arg Phe Arg Gly Ser Gly Ser Gly Thr Asp Phe Thr
210                 215                 220

Leu Thr Ile Ser Ser Val Gln Asp Glu Asp Leu Ala Phe Tyr Tyr Cys
225                 230                 235                 240

Gln Gln Trp Tyr Asp Tyr Pro Tyr Thr Phe Gly Ala Gly Thr Lys Val
                245                 250                 255

Glu Ile Lys

<210> SEQ ID NO 7
<211> LENGTH: 31
<212> TYPE: DNA
<213> ORGANISM: Artificial sequence
<220> FEATURE:
<223> OTHER INFORMATION: A primer for amplifying the gene cassette
      flanked by upstream of nucleotides 117005 and downstream of
      nucleotides 132096 in the context of a wild type genome.

<400> SEQUENCE: 7
ctagctagct tataaaaggc gcgtcccgtg g                                      31

<210> SEQ ID NO 8
<211> LENGTH: 25
<212> TYPE: DNA
<213> ORGANISM: Artificial sequence
```

```
<220> FEATURE:
<223> OTHER INFORMATION: A primer for amplifying the gene cassette
      flanked by upstream of nucleotides 117005 and downstream of
      nucleotides 132096 in the context of a wild type genome.

<400> SEQUENCE: 8
gctctagatt gcgacgcccc ggctc                                          25

<210> SEQ ID NO 9
<211> LENGTH: 35
<212> TYPE: DNA
<213> ORGANISM: Artificial sequence
<220> FEATURE:
<223> OTHER INFORMATION: A primer for amplifying the gene cassette
      flanked by upstream of nucleotides 117005 and downstream of
      nucleotides 132096 in the context of a wild type genome.

<400> SEQUENCE: 9
ccttaattaa ggttaccacc ctgtagcccc gatgt                               35
```

CONSTRUCTION OF ONCOLYTIC HERPES SIMPLEX VIRUSES (OHSV) OBLIGATE VECTOR AND CONSTRUCTS FOR CANCER THERAPY

CROSS-REFERENCE TO RELATED APPLICATION

This application is a U.S. National Stage Application under 35 U.S.C. § 371 of International Application No. PCT/CN2016/080025, filed Apr. 22, 2016, the contents of which is hereby incorporated by reference in its entirety into the present disclosure.

SEQUENCE LISTING

The instant application contains a Sequence Listing which has been filed electronically in ASCII format and is hereby incorporated by reference in its entirety. Said ASCII copy, created on Dec. 4, 2018, is named 271438-US_Seqlst.txt and is 8858 bytes in size.

TECHNICAL FIELD

The present disclosure relates generally to the treatment of cancer using oncolytic herpes simplex viruses (oHSV). In particular, the disclosure relates to the preparation of an obligate HSV vector that can carry and express multiple genes encoding immunostimulatory and/or immunotherapeutic agents. The present disclosure also relates to an innovatively designed genome that can function as a vector that can carry and express multiple therapeutic genes for effective cancer therapy.

BACKGROUND

Oncolytic herpes simplex viruses (oHSV) are being extensively investigated for treatment of solid tumors. As a group, they pose many advantages over traditional cancer therapies (Markert et al., 2000; Russell et al., 2012; Shen and Nemunaitis, 2006). Specifically, oHSV usually embody a mutation that makes them susceptible to inhibition by some aspect of innate immunity. As a consequence they replicate in cancer cells in which one or more innate immune responses to infection are compromised but not in normal cells in which the innate immune responses are intact. oHSV are usually delivered directly into the tumor mass in which the virus can replicate. Because it is delivered to the target tissue rather than systemically, there are no side effect characteristics of anti-cancer drugs. Viruses characteristically induce adaptive immune responses that curtail their ability to be administered multiple times. oHSV has been administered to tumors multiple times without evidence of loss of potency or induction of adverse reaction such as inflammatory responses. HSV are large DNA viruses capable of incorporating into their genomes foreign DNA and to regulate the expression of these gene on administration to tumors. The foreign genes suitable for use with oHSV are those that help to induce an adaptive immune response to the tumor.

The defect in overcoming the cellular innate immune response determines the range of tumors in which the virus exhibits its oncolytic oHSV as an anti-cancer agent. The more extensive the deletions the more restrictive is the range of cancer cells in which the oHSV is effective depends on the function of the deleted viral gene. Most newer oHSV incorporate at least one cellular gene to bolster its anti-cancer activity (Cheema et al., 2013; Goshima et al., 2014; Markert et al., 2012; Walker et al., 2011).

It is convenient to consider separately the structure of the oHSV referred to as the backbone and the foreign genes appropriate for insertion into the backbone. As noted above the structure of the backbone determines the range of susceptible cancers. The foreign genes cause the host to see the cancer cells as legitimate targets of adaptive immune response.

The HSV-1 genome consists of two covalently linked components, designated L and S. Each component consists of unique sequences ($U_L$ for the L component, $U_S$ for the S component) flanked by inverted repeats. The inverted repeats of the L component are designated as ab and b'a'. The inverted repeats of the S component are designated as a'c' and ca. Inverted repeats b'a' and a'c' constitute an internal inverted repeat region. The inverted repeats regions of both L and S components are known to contain two copies of five genes encoding proteins designated ICP0, ICP4, ICP34.5, ORF P and ORF O, respectively and large stretches of DNA that are transcribed but do not encode proteins.

Historically the viruses tested in cancer patients fall into 3 different designs. The first one was based on the evidence that deletion of the ICP34.5 gene significantly attenuated the virus (Andreansky et al., 1997; Chou et al., 1995; Chou et al., 1990; Chou and Roizman, 1992) To insure its safety for treatment of malignant glioblastomas, G207, the first virus tested in patients was further attenuated by an additional mutation in the gene encoding the viral ribonucleotide reductase (Mineta et al., 1995). G207 carrying mutations in both the ICP34.5 and the ribonucleotide reductase genes was too attenuated and was shut off in cancer cells expressing a wild-type protein kinase R (Smith et al., 2006).

The second design was based on the demonstration that if a viral protein designated $U_S11$ is expressed early in infection it compensates in part for the absence of ICP34.5 and recoups ability to grow in cells expressing a wild-type protein kinase R (Cassady et al., 1998a). The design of the backbone of this virus follows that published by Cassady et al (Cassady et al., 1998b) in that the $U_S12$ gene and the promoter of $U_S11$ are deleted. As a consequence $U_S11$ is expressed as an immediate early gene rather than as a late gene.

The backbone of the third virus initially designated R7020 and later renamed NV1020 was the result of modifications of a spontaneous mutant that was initially tested as a live attenuated virus vaccine (Meignier et al., 1988; Weichselbaum et al., 2012). This mutant lacked the internal inverted repeats (consisting of b'a' and a'c', encoding one copy of the genes ICP0, ICP4, ICP34.5, ORF P and ORF O) and the genes encoding $U_L56$ and $U_L24$. In addition it contained bacterial sequences and since it was intended as a vaccine it also contained the genes encoding several HSV-2 glycoproteins. R7020 was extensively tested in patients in liver metastases from colon cancer. In addition it was tested in; head and neck epithelial squamous cell carcinoma and prostate adenocarcinoma xenografts in athymic nude mice and in bladder tumor models (Cozzi et al., 2002; Cozzi et al., 2001; Currier et al., 2005; Fong et al., 2009; Geevarghese et al., 2010; Kelly et al., 2008; Kemeny et al., 2006; Wong et al., 2001).

The success of the oHSV based therapy hinges on the extent of destruction of cancer cells. Early in the development of oHSV it was recognized that that HSV alone could not kill all cancer cells in a solid tumor and that it is unlikely that oHSV treatment could effectively eliminate all cancer cells and that destruction of tumors by oHSV in clinical trials had to involve an adaptive immune response to the tumor. Further studies have shown that the antitumor immune response generated by the infected tumor cell debris could be augmented by incorporation of cytokines. Comparison of oHSV bereft of cytokine gene with oHSV incorporating an immunostimulatory cytokine confirmed this hypothesis (Andreanski et al.) and led ultimately to the incorporation of GM-CSF into oHSV developed for treatment of melanoma (Andtbacka et al., 2015).

The safety profile of oHSV hinges on the deletions of genes that disable one or more viral function that block host innate immune responses to infection. Analyses of the published data suggest that the oHSV in clinical trials carried out to date are over attenuated and could be improved (Miest and Cattaneo, 2014).

Incorporation of genes encoding immunostimulatory cytokines enhances the immune response to the tumor but does no effectively enhance the cytotoxicity caused by T cells that is critical for anti-tumor effects. Tumors co-opt PD-1 and CTLA-4 inhibitory pathways to silence the immune system. PD-1 expresses on activated T cells and other hematopoietic cells while CTLA-4 expresses on activated T cells including regulatory T cells (Fife and Pauken, 2011; Francisco et al., 2010; Keir et al., 2008; Krummel and Allison, 1995; Walunas et al., 1994). Tumors employ PD-1 and CTLA-4 inhibitory pathway to evade the host immune response. To maximize anti-tumor responses it is essential to activate cytotoxic T cells by neutralizing PD-1 by anti-PD1 antibody and in some instances neutralize CTLA4 which present on the surface of T cells (Topalian et al., 2015). While systemic administration of single chain antibody to PD-1 or CTLA4 is effective in enhancing the therapeutic effects oHSV, it is frequently associated with side effects and cannot be administered more than a limited number of times.

Thus there are pressing clinical needs to develop a strategy for developing a safe but more potent oHSV and to combine its administration with that of immunotherapeutic agents.

SUMMARY

An aspect of the disclosure relates to a modified Herpes Simplex Virus type 1 (also referred to as HSV-1, obligate vector, or vector, HSV-1 virus(es) hereinafter) comprising a modified HSV-1 genome. The modification comprises a deletion between the promoter of $U_L56$ gene and the promoter of $U_S1$ of a wild-type HSV-1 genome such that (i) one copy of all double-copy genes is absent and (ii) sequences required for expression of all existing open reading frames (ORFs) in the viral DNA after the deletion are intact.

Another aspect of the disclosure provides an oncolytic Herpes Simplex Virus type 1 (HSV-1) construct, comprising (i) sequences required for expression of all single-copy open reading frames (ORFs) in the viral genome; (ii) only one copy of each of all double-copy genes in the viral genome and (iii) one copy of duplicated DNA encoding noncoding RNAs.

A further aspect of the disclosure relates to a recombinant oncolytic Herpes Simplex Virus type 1 (HSV-1) comprising (a) a modified HSV-1 genome wherein the modification comprises a deletion between the promoter of $U_L56$ gene and the promoter of $U_S1$ gene of a wild-type HSV-1 genome such that (i) one copy of all double-copy genes is absent and (ii) sequences required for expression of all existing open reading frames (ORFs) in the viral DNA after the deletion are intact; and (b) a heterologous nucleic acid sequence encoding an immunostimulatory and/or immunotherapeutic agent, wherein the heterologous nucleic acid sequence is stably incorporated into at least the deleted region of the modified HSV-1 genome.

A further aspect of this disclosure is that the virus vector comprising one copy of all open reading frames, that is $U_L1$ through $U_L56$ and $U_S1$ through $U_S12$ and including the "a" sequences at the ends of the genome is an obligate vector in that by itself it cannot replicate in the highly susceptible Vero cells. The vector can replicate following insertion of DNA comprising (a) cellular DNA coding or non-coding sequences or (b) viral DNA consisting of non-coding sequences. The total amount of DNA that can be tolerated by the obligate vector is at least 15 KB or as much as 22 Kb.

A further aspect relates to a pharmaceutical composition comprising an effective amount of the recombinant oncolytic HSV-1 of the present disclosure and a pharmaceutically acceptable carrier. The composition is formulated for, for example, intratumoral administration.

A further aspect relates to a method of treating cancer comprising administering to a subject in need thereof an effective amount of the recombinant oncolytic HSV-1 or the pharmaceutical composition of the present disclosure. Furthermore, this disclosure relates to the use of the recombinant oncolytic HSV-1 of the disclosure for use in a method of treating cancer.

Yet another aspect of the disclosure relates to a use of the recombinant oncolytic HSV-1 or the pharmaceutical composition of the present disclosure in the preparation of an anti-cancer drug.

BRIEF DESCRIPTION OF DRAWINGS

These and other aspects and advantages of the present disclosure are obvious from the following description described in detail with reference to the accompanied drawings, in which.

DETAILED DESCRIPTION

Definitions

Figure 1:
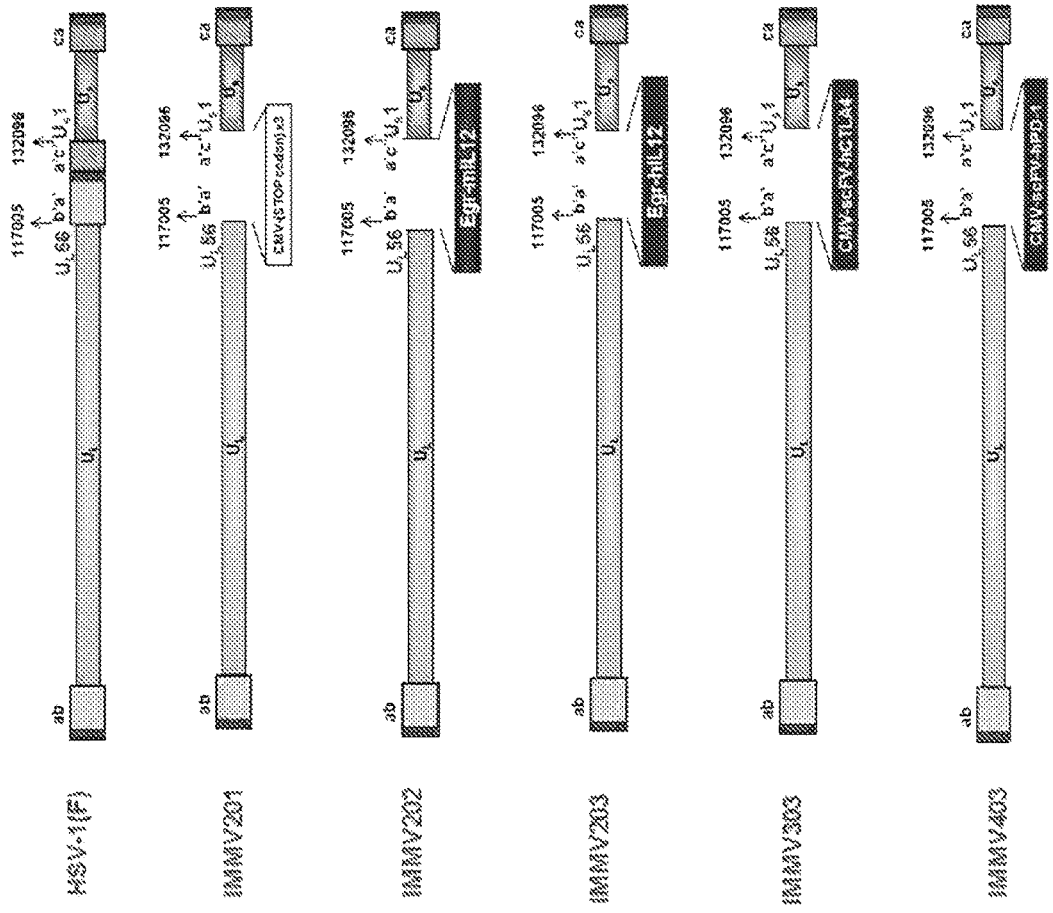
FIG. 1: schematic representations of HSV-1 viruses. HSV-1, genome structure of wild-type HSV-1, showing internal inverted repeat region b'a'-a'c' located between bp117005 and bp132096; IMMV201, genome structure of oHSV-1, also called obligate vector; IMMV202, oHSV-1 expressing murine IL 12; IMMV203, oHSV-1 expressing human IL 12; IMMV303, oHSV-1 expressing human CTLA-4 scFv; IMMV403, oHSV-1 expressing human PD-1 scFv.

It is to be noted that the term "a" or "an" entity refers to one or more of that entity; for example, "a recombinant oncolytic HSV-1," is understood to represent one or more recombinant oncolytic HSV-1 viruses. As such, the terms "a" (or "an"), "one or more," and "at least one" can be used interchangeably herein.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present disclosure.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art.

As used herein, an "antibody" or "antigen-binding polypeptide" refers to a polypeptide or a polypeptide complex that specifically recognizes and binds to one or more antigens. An antibody can be a whole antibody and any antigen binding fragment or a single chain thereof. Thus the term "antibody" includes any protein or peptide containing molecule that comprises at least a portion of an immunoglobulin molecule having biological activity of binding to the antigen. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein. The term antibody also encompasses polypeptides or polypeptide complexes that, upon activation, possess antigen-binding capabilities.

The terms "antibody fragment" or "antigen-binding fragment", as used herein, is a portion of an antibody such as F(ab')$_2$, F(ab)$_2$, Fab', Fab, Fv, scFv and the like. Regardless of structure, an antibody fragment binds with the same antigen that is recognized by the intact antibody. The term "antibody fragment" includes aptamers, spiegelmers, and diabodies. The term "antibody fragment" also includes any synthetic or genetically engineered protein that acts like an antibody by binding to a specific antigen to form a complex.

Antibodies, antigen-binding polypeptides, variants, or derivatives thereof of the disclosure include, but are not limited to, polyclonal, monoclonal, multispecific, human, humanized, primatized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a VK or VH domain, fragments produced by a Fab expression library, and anti-idiotypic (anti-Id) antibodies (including, e.g., anti-Id antibodies to LIGHT antibodies disclosed herein). Immunoglobulin or antibody molecules of the disclosure can be of any type (e.g., IgG, IgE, IgM, IgD, IgA, and IgY), class (e.g., IgGI, IgG2, IgG3, IgG4, IgA1 and IgA2) or subclass of immunoglobulin molecule.

By "specifically binds" or "has specificity to," it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

As used herein, "cancer" or "tumor" as used interchangeably herein is meant to a group of diseases which can be treated according to the disclosure and involve abnormal cell growth with the potential to invade or spread to other parts of the body. Not all tumors are cancerous; benign tumors do not spread to other parts of the body. Possible signs and symptoms include: a new lump, abnormal bleeding, a prolonged cough, unexplained weight loss, and a change in bowel movements among others. There are over 100 different known cancers that affect humans. The present disclosure is preferably applicable to solid tumors. Non-limiting examples of cancer or tumor are bladder cancer, basal cell carcinoma, cholangiocarcinoma, colon cancer, endometrial cancer, esophageal cancer, Ewing's sarcoma, prostate cancer, gastric cancer, glioma, hepatocellular carcinoma, Hodgkin lymphoma, laryngeal carcinoma, liver cancer, lung cancer, melanoma, mesothelioma, pancreatic cancer, rectal cancer, renal cancer, thyroid cancer, malignant peripheral nerve cell tumors, malignant peripheral nerve sheath tumors (MPNST), cutaneous and plexiform neurofibromas, leiomyoadenomatoid tumor, fibroids, uterine fibroids, leiomyosarcoma, papillary thyroid cancer, anaplastic thyroid cancer, medullary thyroid cancer, follicular thyroid cancer, hurthle cell carcinoma, thyroid cancer, ascites, malignant ascites, mesothelioma, salivary gland tumors, mucoepidermoid carcinoma of the salivary gland, acinic cell carcinoma of the salivary gland, gastrointestinal stromal tumors (GIST), tumors that cause effusions in potential spaces of the body, pleural effusions, pericardial effusions, peritoneal effusions aka ascites, giant cell tumors (GCT), GCT of bone, pigmented villonodular synovitis (PVNS), tenosynovial giant cell tumor (TGCT), TCGT of tendon sheath (TGCT-TS), and other sarcomas. In preferable embodiment, the present disclosure is used to treat esophageal cancer, lung cancer, prostate cancer, or bladder cancer.

As used herein, the terms "treat" or "treatment" refer to both therapeutic treatment and prophylactic or preventative measures, wherein the object is to prevent or slow down (lessen) an undesired physiological change or disorder, such as the progression of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sport, or pet animals such as dogs, cats, guinea pigs, rabbits, rats, mice, horses, cattle, cows, and so on.

As used herein, phrases such as "to a patient in need of treatment" or "a subject in need of treatment" includes subjects, such as mammalian subjects, that would benefit from administration of an antibody or composition of the present disclosure used, e.g., for detection, for a diagnostic procedure and/or for treatment.

It will also be understood by one of ordinary skill in the art that modified genomes as disclosed herein may be modified such that they vary in nucleotide sequence from the modified polynucleotides from which they were derived. For example, a polynucleotide or a nucleotide sequence derived from a designated DNA sequence may be similar, e.g., have a certain percent identity to the starting sequence, e.g., it may be 60%, 70%, 75%, 80%, 85%, 90%, 95%, 98%, or 99% identical to the starting sequence.

Furthermore, nucleotide or amino acid substitutions, deletions, or insertions leading to conservative substitutions or changes at "non-essential" amino acid regions may be made. For example, a polypeptide or amino acid sequence derived from a designated protein may be identical to the starting sequence except for one or more individual amino acid substitutions, insertions, or deletions, e.g., one, two, three, four, five, six, seven, eight, nine, ten, fifteen, twenty or more individual amino acid substitutions, insertions, or deletions. In certain embodiments, a polypeptide or amino acid sequence derived from a designated protein has one to five, one to ten, one to fifteen, or one to twenty individual amino acid substitutions, insertions, or deletions relative to the starting sequence.

The antibodies can be detectably labeled by coupling it to a chemiluminescent compound. The presence of the chemiluminescent-tagged antigen-binding polypeptide is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Modified HSV-1 Obligate Vector

In one aspect, the disclosure is provided a HSV-1 virus comprising a modified HSV-1 genome, also called HSV-1 obligate vector. The HSV-1 genome consists of two covalently linked components, designated L and S. Each component consists of unique sequences ($U_L$ for the L component, $U_S$ for the S component) flanked by inverted repeats. The inverted repeats of the L component are designated as ab and b'a'. The inverted repeats of the S component are designated as a'c' and ca. The inverted repeats regions contain double-copy of transcriptional units. There are at least five open reading frames known in the art that have double copies, the proteins of which are designated ICP0, ICP4, ICP34.5, ORF P and ORF O, respectively. The inverted repeats b'a' and a'c' (b'a'-a'c') are joined to form an internal inverted repeat region. In contrast, the inverted repeats ab and ca are herein referred to as external repeat regions.

In one embodiment of the present disclosure, the modification comprises a deletion between the promoter of $U_L56$ gene and the promoter of $U_S1$ gene of a wild-type HSV-1 genome. In effect the sequences deleted include the following:

(a) Single copies of transcriptional units encoding at least 5 proteins (ICP0, ICP4, ICP34.5, ORF-O and ORF-P), all other open reading frames remain.
(b) Transcriptional units that are contained entirely within the b'a'-a'c' sequence.
(c) Transcriptional units that are initiated in the unique region but which extend into the deleted region.

In the present disclosure, the deletion is carried out in a precise manner to make sure that sequences required for expression of all existing open reading frames (ORFs) in the viral DNA after the deletion are intact. In this context, "sequences required for expression of all existing open reading frames" include the ORFs themselves and regulating sequences necessary for expression of each ORF such as promoters and enhancers, to ensure the expression of the ORFs are successful and the proteins so translated are functional. By "intact" it means the sequences so defined are at least functional but it does not mean the sequences have to be 100% percent identical to the naturally occurring sequences. The sequences may slightly vary in nucleotide sequence from naturally occurring sequences by including for example conservative substitutions or changes at "non-essential" regions. In this context, the sequences may be 90%, 95%, 98%, or 99% identical to the naturally occurring sequences.

It will be appreciated by a skilled person in the art that the exact starting and ending positions of the nucleotides to be deleted according to the present disclosure depend on the strains and genome isomers of the HSV-1 virus and can be easily determined by known techniques in the art. It should be understood that the present disclosure is not intended to be limited to any specific genome isomers nor strains of a HSV-1 virus. In an embodiment, the deletion causes the excision of nucleotides 117005 to 132096 in the genome. It also will be appreciated by the person skilled in the art that other strains are also possible as long as the genome DNA is sequenced. Sequencing technologies are easily available in literature and on market. For example, in another embodiment, the deletion may be performed on a HSV-1 strain 17, the genome of which is available by GenBank Accession No. NC_001806.2. In another embodiment, the deletion may be performed on a strain KOS 1.1, the genome of which is available by GenBank Accession No. KT899744. In yet another embodiment, the deletion may be performed on a strain F, the genome of which is available by GenBank Accession No. GU734771.1.

In some embodiments, the deletion is precisely performed at predetermined positions such that an excision of a DNA fragment starting from the promoter of the last known gene in the L component (such as $U_L56$) to the promoter sequence of the first known gene in the S component (such as $U_S1$) is achieved. In this way, all the ORFs of from $U_L1$ to $U_L56$ genes in the $U_L$ component and of from $U_S1$ to $U_S12$ in the $U_S$ component as well as sequence required for the expression of the ORFs are intact. The precise excision and the preservation of sequences required for expression of all existing open reading frames (ORFs) in the viral DNA after the deletion has a lot of advantages. By "preservation" it means the modified vector contains all genes in the unique sequences ($U_L$ and $U_S$) and only one copy of all double-copy genes, e.g., genes for ICP0, ICP4, ICP34.5, ORF P and ORF O. It should be noted that a large fraction of the delete sequences does not encode proteins, but are duplicated non-coding sequences interspaced between the deleted region, e.g., introns of ICP0, LAT domain, "a" sequences and etc. The obligate vector of the invention is intended to include also only one copy of the duplicated non-coding sequences.

The preservation of all ORFs provides a stronger virus, either before or after incorporation of inserted foreign genes, that is to the maximum extent resistant to environmental factors, such as temperatures, pressures, UV light, and etc. It also maximizes the range of cancer cells in which the oncolytic HSV-1 is effective.

Various genetic manipulation methods known in the art can be used to obtain the modified HSV-1 vector as described in the present disclosure. For example, bacterial artificial chromosomes (BAC) technology is used. See, for example, Horsburgh B C, Hubinette M M, Qiang D, et al. Allele replacement: an application that permits rapid manipulation of herpes simplex virus type 1 genome. *Gene Ther,* 1999, 6(5):922-30. As another example, COS plasmid can be used with the present disclosure. See, for example, van Zijl M., Quint W, Briaire J, et al. Regeneration of herpes viruses from molecularly cloned subgenomic fragments. *J Virol,* 1988, 62(6):2191-5.

A key property of the construct described herein is that it acts as an obligate vector. The definition applicable in such constructs is that they do not multiply in susceptible cells but do multiply following insertion of viral or cellular DNA sequences and therefore acts as vectors for expression genes inserted into the vector sequences.

Recombinant Oncolytic HSV-1 Virus

The amount of foreign DNA sequences that can be inserted into the wild-type virus is limited because it interferes with the packaging of the DNA into virions. The precise deletion in the designated region provides an ideal space for insertion of foreign DNA sequences. According to an embodiment of the present disclosure, the deletion removes at least 15 Kbp of the oncolytic virus vector such that a similar amount of foreign DNA sequences can accommodate. Other studies have shown that wild type genomes tolerate an additional 7 KB of DNA.

Therefore, in another aspect, the present disclosure provide a recombinant oncolytic Herpes Simplex Virus type 1 (HSV-1) comprising (a) a modified HSV-1 genome wherein the modification comprises a deletion between the promoter of $U_L56$ gene and the promoter of $U_S1$ gene of a wild-type HSV-1 genome such that (i) one copy of all double-copy genes is absent and (ii) sequences required for expression of all existing open reading frames (ORFs) in the viral DNA after the deletion are intact; and (b) a heterologous nucleic acid sequence encoding an immunostimulatory and/or immunotherapeutic agent, wherein the heterologous nucleic acid sequence is stably incorporated into at least the deleted region of the modified HSV-1 genome.

In an embodiment, the recombinant oncolytic HSV-1 comprises a heterologous nucleic acid sequence encoding an immunostimulatory agent. In some embodiments, the immunostimulatory agent is selected from a group consisting of GM-CSF, IL 2, IL 5, IL 12, IL 15, IL 24 and IL 27. In an embodiment, the immunostimulatory agent is IL 12. In an embodiment, the immunostimulatory agent is a human or humanized IL 12. In an embodiment, the immunostimulatory agent is a murine IL 12. In another embodiment, the immunostimulatory agent is IL 15.

In an embodiment, the recombinant oncolytic HSV-1 comprises a heterologous nucleic acid sequence encoding an immunotherapeutic agent. In some embodiments, the immunotherapeutic agent is selected from an anti-PD-1 agent and an anti-CTLA-4 agent. In an embodiment, the immunotherapeutic agent is an anti-PD-1 agent. In another embodiment, the immunotherapeutic agent is an anti-CTLA-4 agent.

Where only one heterologous nucleic acid sequence encoding an immunostimulatory or immunotherapeutic agent is inserted, the heterologous nucleic acid sequence is preferably incorporated into the deleted region of the genome. In an embodiment, the heterologous nucleic acid sequence has a length similar to that of the deleted region. In an embodiment, the heterologous nucleic acid sequence has a length 20% longer or shorter than that of the deleted region. In another embodiment, the heterologous nucleic acid sequence has a length 15%, 10%, 5%, 4%, 3%, 2%, or 1% longer or shorter than that of the deleted region.

In an embodiment, the heterologous nucleic acid sequence has a length of less than about 18 Kbp, about 17 Kbp, or about 16 Kbp. In an embodiment, the heterologous nucleic acid sequence has a length of more than about 10 Kbp, 11 Kbp, 12 Kbp, 13 Kbp, or 14 Kbp. In an embodiment, the heterologous nucleic acid sequence has a length between about 14 Kbp and about 16 Kbp. In an embodiment, the heterologous nucleic acid sequence has a length of about 15 Kbp.

In some embodiments, the recombinant oncolytic HSV-1 comprises at least two heterologous nucleic acid sequences encoding immunostimulatory and/or immunotherapeutic agents. In some embodiments, the recombinant oncolytic HSV-1 comprises heterologous nucleic acid sequences encoding two different immunostimulatory agents. For example, in one embodiment, the recombinant oncolytic HSV-1 comprises heterologous nucleic acid sequences encoding both IL-12 and GM-CSF. In another embodiment, the recombinant oncolytic HSV-1 comprises heterologous nucleic acid sequences encoding both IL 15 and GM-CSF. In a further embodiment, the recombinant oncolytic HSV-1 comprises heterologous nucleic acid sequences encoding both IL 12 and IL 15.

In some embodiments, the recombinant oncolytic HSV-1 comprises heterologous nucleic acid sequences encoding two different immunotherapeutic agents. In one embodiment, for example, the recombinant oncolytic HSV-1 comprises heterologous nucleic acid sequences encoding both an anti-PD-1 agent and an anti-CTLA-4 agent.

In some embodiments, the recombinant oncolytic HSV-1 comprises heterologous nucleic acid sequences encoding three different immunostimulatory and/or immunotherapeutic agents. For example, in an embodiment, the recombinant oncolytic HSV-1 comprises heterologous nucleic acid sequences encoding IL 12, an anti-CTLA4 agent and an anti-PD-1 agent.

Where more than one heterologous nucleic acid sequences encoding immunostimulatory and/or immunotherapeutic agents are incorporated, a first heterologous nucleic acid sequences is preferably inserted into the deleted region of the genome. A second or further heterologous nucleic acid sequences may be inserted into the L component of the genome. In an embodiment, a second heterologous nucleic acid sequence is inserted between the $U_L3$ and $U_L4$ genes of the L component. In an embodiment, a second heterologous nucleic acid sequence is inserted between the $U_L37$ and $U_L38$ genes of the L component.

In an embodiment, a first heterologous nucleic acid sequence is inserted into the deleted region of the genome and a second heterologous nucleic acid sequence is inserted between the $U_L3$ and $U_L4$ genes. In an embodiment, a first heterologous nucleic acid sequence is inserted into the deleted internal inverted repeat region of the genome and a second heterologous nucleic acid sequence is inserted between the $U_L37$ and $U_L38$ genes of the L component. In an embodiment, a first heterologous nucleic acid sequence is inserted into the deleted internal inverted repeat region of the genome, a second heterologous nucleic acid sequence is inserted between the $U_L3$ and $U_L4$ genes, and a third heterologous nucleic acid sequence is inserted between the $U_L37$ and $U_L38$ genes of the L component.

In an embodiment, the first heterologous nucleic acid sequence encodes IL 12. In an embodiment, the second heterologous nucleic acid sequence encodes an anti-CTLA4 agent or an anti-PD-1 agent. In an embodiment, the third heterologous nucleic acid sequence encodes an anti-PD-1 agent or an anti-CTLA4 agent.

It will be appreciated that the insertions of the one or more heterologous nucleic acid sequences into the oncolytic HSV-1 genome do not interfere the expression of native HSV-1 genes and the heterologous nucleic acid sequences are stably incorporated into the modified HSV-1 genome such that functional expressions of the heterologous nucleic acid sequences can be expected.

A recombinant gene encoding the immunostimulatory and/or immunotherapeutic agents contains nucleic acid encoding a protein along with regulatory elements for protein expression. Generally, the regulatory elements that are present in a recombinant gene and selected on the basis of the host cells to be used for expression that is operably-linked to the nucleic acid sequence to be expressed include a transcriptional promoter, a ribosome binding site, and a terminator. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the virus is introduced into the host cell). The term "regulatory sequence" is intended to include promoters, enhancers and other expression control elements (e.g., polyadenylation signals). Regulatory sequences include those that direct constitutive expression of a nucleotide sequence in many types of host cell and those that direct expression of the nucleotide sequence only in certain host cells (e.g., tissue-specific regulatory sequences).

A newly found regulatory sequence is insulator which includes a class of DNA elements found on cellular chromosomes that protect genes in one region of a chromosome from the regulatory influence of another region. Amelio et al. found a 1.5-kb region containing a cluster of CTCF motifs in the LAT region possesses insulator activities, specifically, enhancer blocking and silencing (Amelio et al., A Chromatin Insulator-Like Element in the Herpes Simplex Virus Type 1 Latency-Associated Transcript RegionBinds CCCTC-Binding Factor and Displays Enhancer-Blocking and Silencing Activities. *Journal of Virology*, Vol. 80, No. 5, March 2006, p. 2358-2368).

A promoter is defined as a DNA sequence that directs RNA polymerase to bind to DNA and initiate RNA synthesis. A strong promoter is one which causes mRNAs to be initiated at high frequency. A suitable element for processing in eukaryotic cells is a polyadenylation signal. Antibody associated introns may also be present. Examples of expression cassettes for antibody or antibody fragment production are well known in art. (e.g., Persic et al., 1997, *Gene* 187:9-18; Boel et al., 2000, *J Immunol. Methods* 239:153-166; Liang et al., 2001, *J. Immunol. Methods* 247:119-130; Tsurushita et al., 2005, *Methods* 36:69-83.)

Appropriate regulatory elements can be selected by those of ordinary skill in the art based on, for example, the desired tissue-specificity and level of expression. For example, a cell-type specific or tumor-specific promoter can be used to limit expression of a gene product to a specific cell type. In addition to using tissue-specific promoters, local administration of the viruses can result in localized expression and effect. Examples of non-tissue specific promoters that can be used include the early Cytomegalovirus (CMV) promoter (U.S. Pat. No. 4,168,062) and the Rous Sarcoma Virus promoter. Also, HSV promoters, such as HSV-1 IE promoters, can be used. In some embodiments, the promoter is selected from a promoter in following table.

| Promoter | Tumor or Tissue Target |
| --- | --- |
| B-myb | Glioma liver metastasis |
| Nestin | Glioma |
| CEA (Carinoembryonic antigen) | Colon Cancer |
| Albumin | Hepatoma |
| DF3/MUC1 (Mucin 1) | Pancreatic Cancer |
| Caponin | Leiomyosarcoma |

Examples of tissue-specific promoters that can be used in the technology include, for example, the prostate-specific antigen (PSA) promoter, which is specific for cells of the prostate; the desmin promoter, which is specific for muscle cells; the enolase promoter, which is specific for neurons; the beta-globin promoter, which is specific for erythroid cells; the tau-globin promoter, which is also specific for erythroid cells; the growth hormone promoter, which is specific for pituitary cells; the insulin promoter, which is specific for pancreatic beta cells; the glial fibrillary acidic protein promoter, which is specific for astrocytes; the tyrosine hydroxylase promoter, which is specific for catecholaminergic neurons; the amyloid precursor protein promoter, which is specific for neurons; the dopamine beta-hydroxylase promoter, which is specific for noradrenergic and adrenergic neurons; the tryptophan hydroxylase promoter, which is specific for serotonin/pineal gland cells; the choline acetyltransferase promoter, which is specific for cholinergic neurons; the aromatic L-amino acid decarboxylase (AADC) promoter, which is specific for catecholaminergic/5-HT/D-type cells; the proenkephalin promoter, which is specific for neuronal/spermatogenic epididymal cells; the reg (pancreatic stone protein) promoter, which is specific for colon and rectal tumors, and pancreas and kidney cells; and the parathyroid hormone-related peptide (PTHrP) promoter, which is specific for liver and cecum tumors, and neurilemoma, kidney, pancreas, and adrenal cells.

Examples of promoters that function specifically in tumor cells include the stromelysin 3 promoter, which is specific for breast cancer cells; the surfactant protein A promoter, which is specific for non-small cell lung cancer cells; the secretory leukoprotease inhibitor (SLPI) promoter, which is specific for SLPI-expressing carcinomas; the tyrosinase promoter, which is specific for melanoma cells; the stress inducible grp78/BiP promoter, which is specific for fibrosarcoma/tumorigenic cells; the AP2 adipose enhancer, which is specific for adipocytes; the a-1 antitrypsin transthyretin promoter, which is specific for hepatocytes; the interleukin-10 promoter, which is specific for glioblastoma multiform cells; the c-erbB-2 promoter, which is specific for pancreatic, breast, gastric, ovarian, and non-small cell lung cells; the a-B-crystallin/heat shock protein 27 promoter, which is specific for brain tumor cells; the basic fibroblast growth factor promoter, which is specific for glioma and meningioma cells; the epidermal growth factor receptor promoter, which is specific for squamous cell carcinoma, glioma, and breast tumor cells; the mucin-like glycoprotein (DF3, MUC1) promoter, which is specific for breast carcinoma cells; the mtsI promoter, which is specific for metastatic tumors; the NSE promoter, which is specific for small-cell lung cancer cells; the somatostatin receptor promoter, which is specific for small cell lung cancer cells; the c-erbB-3 and c-erbB-2 promoters, which are specific for breast cancer cells; the c-erbB4 promoter, which is specific for breast and gastric cancer; the thyroglobulin promoter, which is specific for thyroid carcinoma cells; the ofetoprotein (AFP) promoter, which is specific for hepatoma cells; the villin promoter, which is specific for gastric cancer cells; and the albumin promoter, which is specific for hepatoma cells. In another embodiment, the TERT promoter or survivin promoter are used.

For example, in some embodiments, heterologous nucleic acid sequences are operably linked to a promoter, for example, a CMV promoter or an Egr promoter. In an embodiment, a nucleotide sequence encoding mIL12 is operably linked to an Egr promoter. In another embodiment, a nucleotide sequence encoding a scFv-anti-hPD1 is operably linked to a CMV promoter.

Immunostimulatory or Immunotherapeutic Agents

In certain embodiments, the oHSV-1 of the present disclosure encodes one or more immunostimulatory agents (also called immune stimulating molecules), including cytokines such as IL-2, IL4, IL-12, GM-CSF, IFNγ, chemokines such as MIP-1, MCP-1, IL-8 and growth factors such as FLT3 ligand.

Alternatively, or in addition, the oHSV-1 of the present disclosure encodes one or more immunotherapeutic agents, for example a PD-1 binding agent (or anti-PD-1 agent), or a CTLA-4 binding agent (or anti-CTLA-4 agent), including antibodies or fragments thereof, for example an anti-PD1 antibody specifically binding to PD-1 or an anti-CTLA-4 antibody specifically binding to CTLA-4. The anti-PD-1 antibody may be a single chain antibody that antagonizes the activity of PD-1. In other embodiments, the oncolytic virus expresses an agent that antagonizes the binding of the PD-1 ligands to the receptor, e.g., anti-PD-L1 and/or PD-L2 antibodies, PD-L1 and/or PD-L2 decoys, or a soluble PD-1 receptor.

The PD-1 signaling pathway plays an important role in tumor-associated immune dysfunction. Infection and lysis of the tumor cells can invoke a highly specific antitumor immune response which kills cells of the inoculated tumor, as well as cells of distant, established, non-inoculated tumors. Tumors and their microenvironments have developed mechanisms to evade, suppress and inactivate the natural anti-tumor immune response. For example, tumors may down-regulate targeted receptors, encase themselves in a fibrous extracellular stromal matrix or up-regulate host receptors or ligands involved in the activation or recruitment of regulatory immune cells. Natural and/or adaptive T regulatory cells (Tregs) have been implicated in tumor-mediated immune suppression. Without wishing to be limited by theory, PD-1 blockade may inhibit Treg activity and improve the efficacy of tumor-reactive CTLs. Further aspects of the technology will be described in further detail below. PD-1 blockade may also stimulate the anti-tumor immune response by blocking the inactivation of T-cells (CTLs and helper) and B-cells.

In one aspect, the present technology provides an oncolytic virus that carries a gene encoding a PD-1 binding agent. Programmed Cell Death 1 (PD-1) is a 50-55 kDa type I transmembrane receptor originally identified by subtractive hybridization of a mouse T cell line undergoing apoptosis (Ishida et al., 1992, Embo J. 11:3887-95). A member of the CD28 gene family, PD-1 is expressed on activated T, B, and myeloid lineage cells (Greenwald et al., 2005, Annu. Rev. Immunol. 23:515-48; Sharpe et al., 2007, Nat. Immunol. 8:239-45). Human and murine PD-1 share about 60% amino acid identity with conservation of four potential N-glycosylation sites and residues that define the Ig-V domain. Two ligands for PD-1 have been identified, PD ligand 1 (PD-L1) and ligand 2 (PD-L2); both belong to the B7 superfamily. PD-L1 is expressed on many cell types, including T, B, endothelial and epithelial cells, and antigen presenting cells. In contrast, PD-L2 is narrowly expressed on professional antigen presenting cells, such as dendritic cells and macrophages.

PD-1 negatively modulates T cell activation, and this inhibitory function is linked to an immunoreceptor tyrosine-based inhibitory motif (ITIM) of its cytoplasmic domain (Parry et al., 2005, Mol. Cell. Biol. 25:9543-53). Disruption of this inhibitory function of PD-1 can lead to autoimmunity. The reverse scenario can also be deleterious. Sustained negative signals by PD-1 have been implicated in T cell dysfunctions in many pathologic situations, such as tumor immune evasion and chronic viral infections.

Host anti-tumor immunity is mainly affected by tumor-infiltrating lymphocytes (TILs) (Galore et al., 2006, Science 313:1960-4). Multiple lines of evidence have indicated that TILs are subject to PD-1 inhibitory regulation. First, PD-L1 expression is confirmed in many human and mouse tumor lines and the expression can be further upregulated by IFN-γ in vitro (Dong et al., 2002, Nat. Med. 8:793-800). Second, expression of PD-L1 by tumor cells has been directly associated with their resistance to lysis by anti-tumor T cells in vitro (Blank et al., 2004, Cancer Res. 64:1 140-5). Third, PD-1 knockout mice are resistant to tumor challenge (Iwai et al., 2005, Int. Immunol. 17:133-44) and T cells from PD-1 knockout mice are highly effective in tumor rejection when adoptively transferred to tumor-bearing mice (Blank et al., supra). Fourth, blocking PD-1 inhibitory signals by a monoclonal antibody can potentiate host anti-tumor immunity in mice (Iwai et al., supra; Hirano et al., 2005, Cancer Res. 65:1089-96). Fifth, high degrees of PD-L1 expression in tumors (detected by immunohistochemical staining) are associated with poor prognosis for many human cancer types (Hamanishi et al., 2007, Proc. Natl. Acad. Sci. USA 104:3360-5).

Oncolytic virotherapy is an effective method to shape the host immune system by expanding T or B cell populations specific for tumor-specific antigens that are released following oncolysis. The immunogenicity of the tumor-specific antigens is largely dependent on the affinity of host immune receptors (B-cell receptors or T-cell receptors) to antigenic epitopes and the host tolerance threshold. High affinity interactions will drive host immune cells through multiple rounds of proliferation and differentiation to become long-lasting memory cells. The host tolerance mechanisms will counterbalance such proliferation and expansion in order to minimize potential tissue damage resulting from local immune activation. PD-1 inhibitory signals are part of such host tolerance mechanisms, supported by following lines of evidence. First, PD-1 expression is elevated in actively proliferating T cells, especially those with terminal differentiated phenotypes, i.e., effector phenotypes. Effector cells are often associated with potent cytotoxic function and cytokine production. Second, PD-L1 is important to maintain peripheral tolerance and to limit overly active T cells locally. Therefore, PD-1 inhibition using a PD-1 binding agent expressed in the tumor microenvironment can be an effective strategy to increase the activity of TIL and stimulate an effective and durable anti-tumor immune response.

Cytotoxic T-lymphocyte antigen 4 (CTLA-4) is a member of the immunoglobulin (Ig) superfamily of proteins. The Ig superfamily is a group of proteins that share key structural features of either a variable (V) or constant (C) domain of Ig molecules. Members of the Ig superfamily include, but are not limited to, the immunoglobulins themselves, major histocompatibility complex (MHC) class molecules (i.e., MHC class I and II), and TCR molecules. T-cells required two types of signals from the antigen presenting cell (APC) for activation and subsequent differentiation to effector function. First, there is an antigen specific signal generated by interactions between the TCR on the T-cell and MHC molecules presenting peptides on the APC. Second, there is an antigen-independent signal that is mediated by the interaction of CD28 with members of the B7 family (B7-1 (CD80) or B7-2 (CD86)). Exactly where CTLA-4 fit into the milieu of immune responsiveness was initially evasive. Murine CTLA-4 was first identified and cloned by Brunet et al. *Nature* 328:267-270 (1987), as part of a quest for molecules that are preferentially expressed on cytotoxic T lymphocytes. Human CTLA-4 was identified and cloned shortly thereafter by Dariavach et al. Eur. J. Immunol. 18:1901-1905 (1988). The murine and human CTLA-4 molecules possess approximately 76% overall sequence homology and approach complete sequence identity in their cytoplasmic domains (Dariavach et al. *Eur. J. Immunol.* 18:1901-1905 (1988)).

Beginning in 1993 and culminating in 1995, investigators began to further delineate the role of CTLA-4 in T-cell stimulation. First, through the use of monoclonal antibodies against CTLA-4, Walunas et al. Immunity 1:405-13 (1994) provided evidence that CTLA-4 can function as a negative regulator of T cell activation.

In connection with cancer, Kwon et al. *PNAS USA* 94:8099-103 (1997) established a syngeneic murine prostate cancer model and examined two distinct manipulations intended to elicit an antiprostate cancer response through enhanced T cell costimulation: (i) provision of direct costimulation by prostate cancer cells transduced to express the B7.1 ligand and (ii) in vivo antibody-mediated blockade of T cell CTLA-4, which prevents T cell down-regulation. It was demonstrated that in vivo antibody-mediated blockade of CTLA-4 enhanced antiprostate cancer immune responses. Also, Yang et al. Cancer Res 57:4036-41 (1997) investigated whether the blockade of the CTLA-4 function leads to enhancement of antitumor T cell responses at various stages of tumor growth. Based on in vitro and in vivo results they found that CTLA-4 blockade in tumor-bearing individuals enhanced the capacity to generate antitumor T-cell responses, but the expression of such an enhancing effect was restricted to early stages of tumor growth in their model. Further, Hurwitz et al. Proc Natl Acad Sci USA 95:10067-71 (1998) investigated the generation of a T cell-mediated antitumor response depends on T cell receptor engagement by major histocompatibility complex/antigen as well as CD28 ligation by B7. Certain tumors, such as the SM1 mammary carcinoma, were refractory to anti-CTLA-4 immunotherapy. Thus, through use of a combination of CTLA-4 blockade and a vaccine consisting of granulocyte-macrophage colony-stimulating factor-expressing SM1 cells, regression of parental SM1 tumors was observed, despite the ineffectiveness of either treatment alone. This combination therapy resulted in long-lasting immunity to SM1 and depended on both CD4(+) and CD8(+) T cells. The findings suggested that CTLA-4 blockade acts at the level of a host-derived antigen-presenting cell.

Anti-PD-1 Agents and Anti-CTLA-4 Agents

In one aspect, the present technology provides an oncolytic virus comprising a heterologous nucleic acid encoding an anti-PD-1 agent and/or an anti-CTLA-4 agent. In some embodiments, the anti-PD-1 agents or the anti-CTLA-4 agents contain an antibody variable region providing for specific binding to a PD-1 or CTLA-4 epitope. The antibody variable region can be present in, for example, a complete antibody, an antibody fragment, and a recombinant derivative of an antibody or antibody fragment. The term "antibody" describes an immunoglobulin, whether natural or partly or wholly synthetically produced. Thus, anti-PD-1 agents or anti-CTLA-4 agents of the present technology include any polypeptide or protein having a binding domain which is specific for binding to a PD-1 or CTLA-4 epitope.

Different classes of antibodies have different structures. Different antibody regions can be illustrated by reference to IgG. An IgG molecule contains four polypeptide chains, two longer length heavy chains and two shorter light chains that are inter-connected by disulfide bonds. The heavy and light chains each contain a constant region and a variable region. A heavy chain is comprised of a heavy chain variable region ($V_H$) and a heavy chain constant region (CH1, CH2 and CH3). A light chain is comprised of a light chain variable region ($V_L$) and a light chain constant region (CL). There are three hypervariable regions within the variable regions that are responsible for antigen specificity. (See, for example, Breitling et al., *Recombinant Antibodies*, John Wiley & Sons, Inc. and Spektrum Akademischer Verlag, 1999; and Lewin, Genes IV, Oxford University Press and Cell Press, 1990.)

The hypervariable regions are generally referred to as complementarity determining regions ("CDR") and are interposed between more conserved flanking regions referred to as framework regions ("FW"). There are four (4) FW regions and three (3) CDRs that are arranged from the NH2 terminus to the COOH terminus as follows: FW1, CDR1, FW2, CDR2, FW3, CDR3, FW4. Amino acids associated with framework regions and CDRs can be numbered and aligned by approaches described by Kabat et al., Sequences of Proteins of Immunological Interest, U.S. Department of Health and Human Services, 1991; C. Chothia and A. M. Lesk, *J Mol Biol* 196(4):901 (1987); or B. Al-Lazikani, et al., *J Mol Biol* 273(4): 27, 1997. For example, the framework regions and CDRs can be identified from consideration of both the Kabat and Chothia definitions. The variable regions of the heavy and light chains contain a binding domain that interacts with an antigen. The two heavy chain carboxyl regions are constant regions joined by disulfide bonding to produce an Fc region. The Fc region is important for providing effector functions. (Presta, *Advanced Drug Delivery Reviews* 58:640-656, 2006.) Each of the two heavy chains making up the Fc region extends into different Fab regions through a hinge region.

The anti-PD-1 agents or the anti-CTLA-4 agents typically contain an antibody variable region. Such antibody fragments include but are not limited to (i) a Fab fragment, a monovalent fragment consisting of the $V_H$, $V_L$, $C_H$ and $C_L$ domains; (ii) a Fab$_2$ fragment, a bivalent fragment comprising two Fab fragments linked by a disulfide bridge at the hinge region; (iii) a Fd fragment consisting of the $V_H$, and $C_H1$ domains; (iv) a Fv fragment consisting of the $V_H$ and $V_L$ domains of a single arm of an antibody; (v) a dAb fragment, which comprises either a $V_H$ or $V_L$ domain; (vi) a scAb, an antibody fragment containing $V_H$ and $V_L$ as well as either $C_1$ or $C_H1$ and (vii) artificial antibodies based upon protein scaffolds, including but not limited to fibronectin type III polypeptide antibodies (e.g., see U.S. Pat. No. 6,703,199). Furthermore, although the two domains of the Fv fragment, $V_L$ and $V_H$, are coded for by separate genes, they can be joined using recombinant methods by a synthetic linker that enables them to be made as a single protein chain in which the $V_L$ and $V_H$ regions pair to form monovalent molecules, known as single chain Fv (scFv). Thus, the antibody variable region can be present in a recombinant derivative. Examples of recombinant derivatives include single-chain antibodies, diabody, triabody, tetrabody, and miniantibody. An anti-PD-1 agent or an anti-CTLA-4 agent can also contain one or more variable regions recognizing the same or different epitopes.

In some embodiments, anti-PD-1 agents or anti-CTLA-4 agents are encoded by an oncolytic virus produced using recombinant nucleic acid techniques. Different anti-PD-1 agents can be produced by different techniques, including, for example, a single chain protein containing a $V_H$ region and $V_L$ region connected by a linker sequence, such as a scFv, and antibodies or fragments thereof; and a multi-chain protein containing a $V_H$ and $V_L$ region on separate polypeptides. Recombinant nucleic acid techniques involve constructing a nucleic acid template for protein synthesis.

Suitable recombinant nucleic acid techniques are well known in the art. (See, for example, Ausubel, Current Protocols in Molecular Biology, John Wiley, 2005; Harlow et al., Antibodies, A Laboratory Manual, Cold Spring Harbor Laboratory, 1988). Recombinant nucleic acid encoding an anti-PD-1 antibody or an anti-CTLA-4 antibody can be expressed in a cell that has been infected with an oncolytic virus and released into the tumor microenvironment upon viral lysis. The cell in effect serves as a factory for the encoded protein.

A nucleic acid comprising one or more recombinant genes encoding for either or both of an anti-PD-1 or anti-CTLA-4 agent $V_H$ region or $V_L$ region can be used to produce a complete protein/polypeptide binding to PD-1/CTLA-4. A complete binding agent can be provided, for example, using a single gene to encode a single chain protein containing a $V_H$ region and $V_L$ region connected by a linker, such as a scFv, or using multiple recombinant regions to, for example, produce both $V_H$ and $V_L$ regions.

Exemplary anti-PD-1 antibodies or anti-CTLA-4 antibodies, or its fragments or derivatives useful for the present disclosure are available in the art. See for example WO 2006/121168, WO 2014/055648, WO 2008/156712, US 2014/0234296, or U.S. Pat. No. 6,984,720.

The oHSV-1 recombined in this disclosure delivers the immune potentiating protein in the tumor precisely where they are needed rather than systemically. Furthermore, by reducing production and most likely also uptake of the proteins in the tumor mass cytotoxic manifestations are likely to be grossly reduced or nonexistent.

Example Anti-PD-1 scFv and Anti-CTLA-4 scFv Sequences 1. anti-mPD-1 scFv-nucleic acid (SEQ ID NO: 1)

```
ATGGGATGGT CATGTATCAT CCTTTTTCTA GTAGCAACTG CAACCGGCGC GCACTCCGAG
GTGCAGCTGG TGCAGTCTGG GGGAGGCGTG GTTCAGCCTG GGAGGTCCCT GAGACTCTCC
TGTGCAGCGT CTGGATTCAC CTTTAGTAGC TATTGGATGA GCTGGGTCCG CCAGGCTCCA
GGGAAGGGGC TGGAGTGGGT CTCAGCTATT AGTGGTAGTG GTGGTAGCAC ATACTACGCA
GACTCCGTGA AGGGCCGGTT CACCATCTCC AGAGACAATT CCAAGAACAC GCTGTATCTG
CAAATGAACA GCCTAAGAGC CGAGGACACG GCCGTATATT ACTGTGCGAA AGAGAACTGG
GGATCGTACT TCGATCTCTG GGGGCAAGGG ACCACGGTCA CCGTCTCCTC AGGTGGCGGA
GGGTCAGGTG GCGGAGGGTC AGGTGGCGGA GGGTCAGGCG TGCACTCCGA CATCGTGATG
ACCCAGTCTC CTTCCACCCT GTCTGCATCT GTAGGAGACA GAGTCACCAT CACTTGCCGG
GCCAGTCAGG GTATTAGTAG CTGGTTGGCC TGGTATCAGC AGAAACCAGG GAGAGCCCCT
AAGGTCTTGA TCTATAAGGC ATCTACTTTA GAAAGTGGGG TCCCATCAAG GTTCAGCGGC
AGTGGATCTG GGACAGATTT CACTCTCACC ATCAGCAGTC TGCAACCTGA AGATTTTGCA
ACTTACTACT GTCAACAGAG TTACAGTACC CCGTGGACGT TCGGCCAGGG GACCAAGCTG
GAAATCAAGA GATGATAA
```

2. anti-mPD-1 scFv-protein (SEQ ID NO: 2)

```
MGWSCIILFL VATATGAHSE VQLVQSGGGV VQPGRSLRLS CAASGFTFSS YWKISWVRQAP
GKGLEWVSAI SGSGGSTYYA DSVKGRFTIS RDNSKNTLYL QMNSLRAEDT AVYYCAKENW
GSYFDLWGQG TTVTVSSGGG GSGGGGSGGG GSGVHSDIVM TQSPSTLSAS VGDRVTITCR
ASQGISSWLA WYQQKPGRAP KVLIYKASTL ESGVPSRFSG SGSGTDFTLT ISSLQPEDFA
TYYCQQSYST PWTFGQGTKL EIKR
```

3. anti-mCTLA-4 scFv-nucleic acid (SEQ ID NO: 5)

```
ATGGGATGGT CATGTATCAT CCTTTTTCTA GTAGCAACTG CAACCCAGAT CCAGCTTCAG
GAGTCAGGAC CTGGCCTGGT GAACCCCTCA CAATCACTGT CCCTCTCTTG CTCTGTCACT
GGTTACTCCA TCACCAGTGG TTATGGATGG AACTGGATCA GGCAGTTCCC AGGGCAGAAG
GTGGAGTGGA TGGGATTCAT ATATTATGAG GGTAGCACCT ACTACAACCC TTCCATCAAG
AGCCGCATCT CCATCACCAG AGACACATCG AAGAACCAGT TCTTCCTGCA GGTGAATTCT
GTGACCACTG AGGACACGGC CACATATTAC TGTGCGAGAC AAACTGGGTA CTTTGATTAC
TGGGGCCAAG GAACCATGGT CACCGTCTCC TCAGGTGGTG GTGGATCAGG TGGAGGCGGA
AGTGGAGGTG GCGGTTCCGA CATCATGATG ACCCAGTCTC CTTCATCCCT GAGTGTGTCA
GCGGGAGAGA AAGCCACTAT CAGCTGCAAG TCCAGTCAGA GTCTTTTCAA CAGTAACGCC
AAAACGAACT ACTTGAACTG GTATTTGCAG AAACCAGGGC AGTCTCCTAA ACTGCTGATC
TATTATGCAT CCACTAGGCA TACTGGGGTC CCTGATCGCT TCAGAGGCAG TGGATCTGGG
```

```
ACGGATTTCA CTCTCACCAT CAGCAGTGTC CAGGATGAAG ACCTGGCATT TTATTACTGT
CAGCAGTGGT ATGACTACCC ATACACGTTC GGAGCTGGGA CCAAGGTGGA AATCAAATGA
TAA
```

4. anti-mCTLA-4 scFv-protein (SEQ ID NO: 6)

```
MGWSCIILFL VATATQIQLQ ESGPGLVNPS QSLSLSCSVT GYSITSGYGW NWIRQFPGQK
VEWMGFIYYE GSTYYNPSIK SRISITRDTS KNQFFLQVNS VTTEDTATYY CARQTGYFDY
WGQGTMVTVS SGGGGSGGGG SGGGGSDIMM TQSPSSLSVS AGEKATISCK SSQSLFNSNA
KTNYLNWYLQ KPGQSPKLLI YYASTRHTGV PDRFRGSGSG TDFTLTISSV QDEDLAFYYC
QQWYDYPYTF GAGTKVEIK
```

Compositions

The oncolytic virus may be prepared in a suitable pharmaceutically acceptable carrier or excipient. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria and fungi.

The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intratumoral and intraperitoneal administration. In this connection, sterile aqueous media that can be employed will be known to those of skill in the art in light of the present disclosure. For example, one dosage may be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologies standards.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared.

Therapies

A further aspect of the disclosure provides a method for treating or alleviating a cancer, comprising administering to a subject in need thereof an effective amount of the recombinant oncolytic HSV-1 virus or the pharmaceutical composition comprising the recombinant oncolytic HSV-1 virus as described above. Equally, the disclosure provides the oncolytic HSV-1 virus as described above for use in a method for treating or alleviating cancer.

In certain embodiments, the recombinant oncolytic HSV-1 virus or the pharmaceutical composition is administered intratumorally. In an embodiment, the HSV-1 virus or the pharmaceutical composition is injected directly to a tumor mass in the form of an injectable solution.

In some embodiments, it may be desirable to combine an oncolytic virus carrying a gene encoding an immunostimulatory and/or immunotherapeutic agent with other agents effective in the treatment of cancer. For example, the treatment of a cancer may be implemented with an oncolytic virus and other anti-cancer therapies, such as anti-cancer agents or surgery. In the context of the present technology, it is contemplated that oncolytic virus therapy could be used in conjunction with chemotherapeutic, radiotherapeutic, immunotherapeutic or other biological intervention.

An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. Anti-cancer agents include biological agents (biotherapy), chemotherapy agents, and radiotherapy agents. More generally, these other compositions would be provided in a combined amount effective to kill or inhibit proliferation of the cell. This process may involve contacting the cells with the expression construct and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent(s).

In some embodiments, the oncolytic virus carrying a gene encoding an immunostimulatory and/or immunotherapeutic agent is combined with an adjuvant. In one embodiment, the adjuvant is an oligonucleotide comprising an unmethylated CpG motif. Unmethylated dinucleotide CpG motifs in bacterial deoxyribonucleic acid (DNA) have advantages for stimulating several immune cells to secrete cytokines for enhancements of innate and adaptive immunity.

The viral therapy may precede or follow the other agent treatment by intervals ranging from minutes to weeks. In embodiments where the other agent and oncolytic virus are applied separately to the cell, one would generally ensure that a significant period of time did not expire between the time of each delivery, such that the agent and virus would still be able to exert an advantageously combined effect on the cell. In such instances, it is contemplated that one may contact the cell with both modalities within about 12-24 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

Constructions of oHSVs Expressing Immunostimulatory or Immunotherapeutic Genes

Construction of Modified oHSV-1 Obligate Vector (IMMV201)

In the generation of obligate vector-IMMV201 through bacterial artificial chromosome (BAC) technology, cassettes of CMV promoter, ATGCAGGTGCAGTAATAGTAA which produces 3 STOP codons was inserted into T-Easy vector. A HSV-1 in prototype (P) arrangement is used. Cassettes flanked by upstream of nucleotides 117005 and downstream of nucleotides 132096 in the context of a wild type genome were PCR amplified from HSV-1 viral genome by two sets of primers respectively (GAAGATCTAAT-ATTTTTATTGCAACTCCCTG, CTAGCTAGCT-TATAAAAGGCGCGTCCCGTGG) and (GCTCTAGATT-GCGACGCCCCGGCTC, CCTTAATTAAGGTTACCACCCTGTAGCCCGATGT) and inserted into the plasmid contains CMV and 3 STOP codon described above, then constructed into pKO5, the gene replacement plasmid to generate pKO-CMV-STOP. IMMV201 was engineered by electroporating pKO-CMV-STOP into *E. coli* RecA+ harboring BAC HSV.

BAC-IMMV201 was Failed to Grow Virus in Mammalian Cells 2-3 µg of the BAC-IMMV201 as constructed above was transfected into Vero cells with 70% confluence by using OptiMEM agency (Life Technologies, Inc.) following its instruction. Incubate the cells at 37° C., 5% of $CO_2$ incubator for 4 hours. Following incubation, replace with 4 ml fresh complete growth medium (5% Newborn Calf Serum/DMEM). There is no any virus plaque appeared in 3-4 days. The experiments have been repeated three times, and no virus plaque was appeared.

Constructions of oHSV-1 Expressing Single Immunostimulatory or Immunotherapeutic Gene (IMMV202, 203, 303, 403)

Cassettes of CMV promoter driving immunostimulatory genes (murine IL12, human IL12) or immunotherapeutic genes (human PD-1 scFV (SEQ ID No. 1 or 3), human CTLA-4 scFV (SEQ ID No. 5) were engineered by electroporating of the pKO-cassettes into *E. coli* RecA+ harboring IMMV201 (shown in FIG. 1).

Constructions of oHSV-1 Expressing Two Immunostimulatory or Immunotherapeutic Genes (IMMV502, 503, 504, 505, 507)

Figure 2:
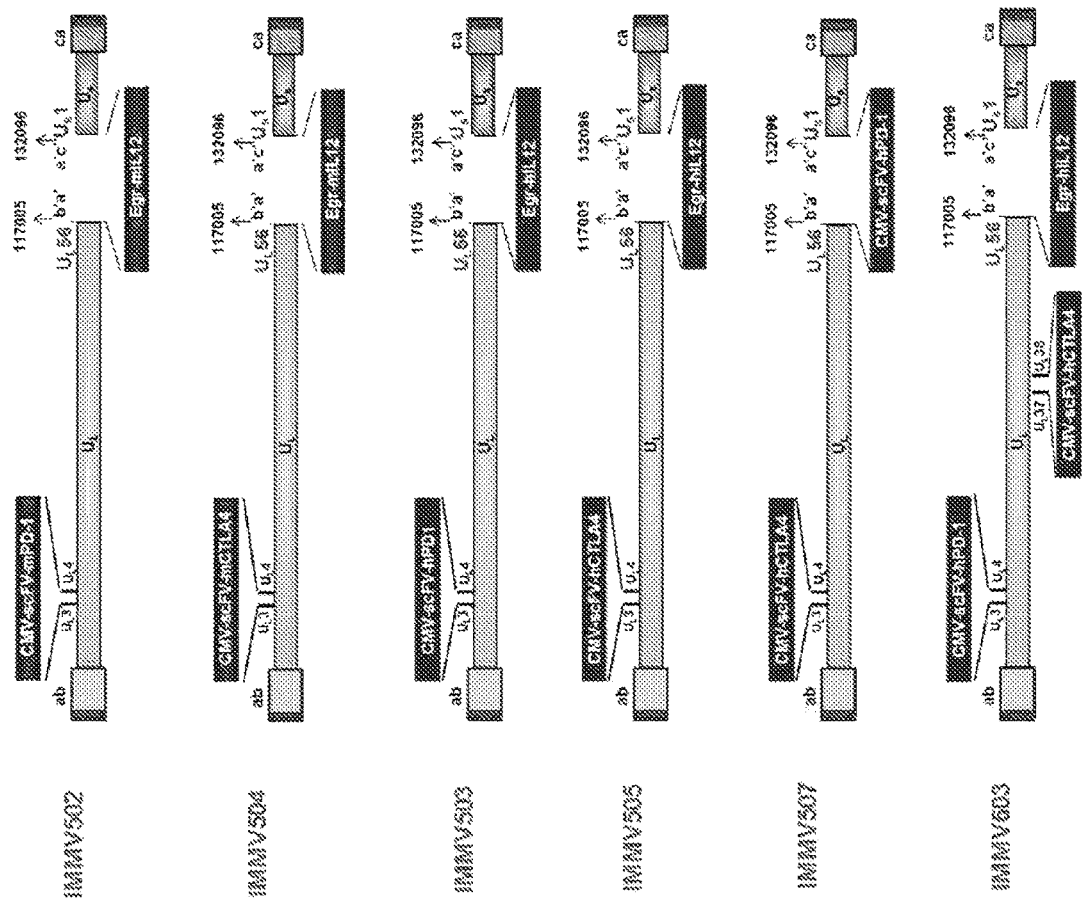
FIG. 2: schematic representations of oncolytic HSV-1 viruses based on the obligate vectors, which express immunostimulatory and/or immunotherapeutic agents. IMMV502, oHSV-1 expressing human anti-PD-1 scFv and murine IL 12; IMMV504, oHSV-1 expressing murine anti-CTLA-4 scFv and murine IL 12; IMMV503, oHSV-1 expressing human anti-PD-1 scFv and human IL 12; IMMV505, oHSV-1 expressing human anti-CTLA-4 scFv and human IL 12; IMMV507, oHSV-1 expressing human anti-CTLA-4 scFv and human anti-PD-1 scFv; IMMV603, oHSV-1 expressing human anti-CTLA-4 scFv, human anti-PD-1 scFv and human IL 12.

Cassettes of CMV promoter driving immunostimulatory genes (IL12) and immunotherapeutic genes (PD-1 scFV, CTLA-4 scFV) were further inserted between UL3 and UL4 genes in the vector of IMMV202, 203, 303, 403 to generate recombinant oHSVs which express combination of immunostimulatory genes (IL12) and immunotherapeutic genes shown in FIG. 2.

Construction of oHSV-1 Expressing One Immunostimulatory Gene and Two Immunotherapeutic Genes (IMMV603)

IMMV603 expressed all three immunostimulatory and immunotherapeutic cDNAs which encoding human IL12, PD-1 scFV, and CTLA-4 scFV by insertion of CTLA-4 scFV between UL37 and UL38 genes in the vector of IMMV503 (shown in FIG. 2).

In Vitro Assays

Expression of PD-1 scFV

Figure 3:
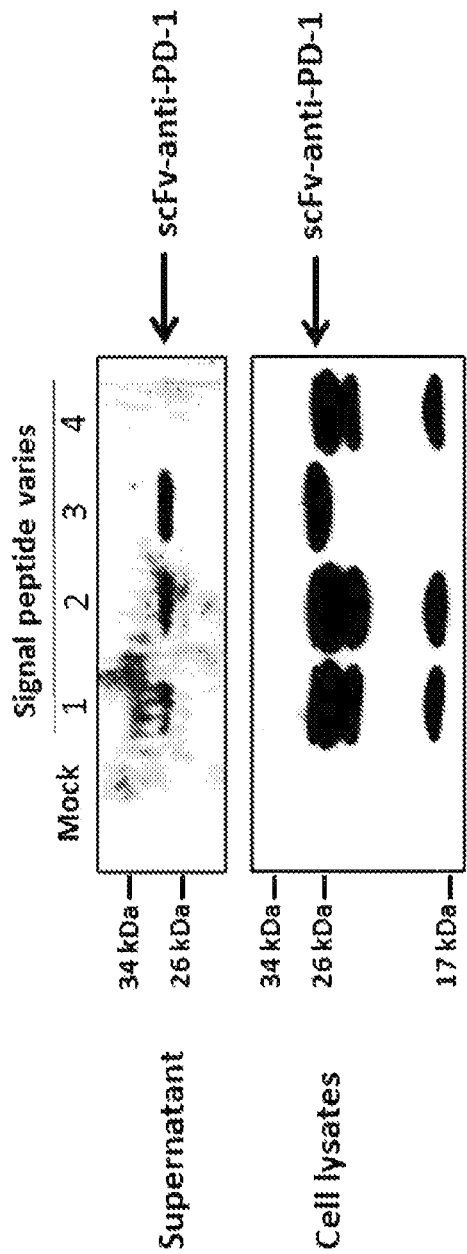
FIG. 3: expression of anti-PD-1 scFv from secretion test constructs. Expression of His-tagged scFv-anti-PD-1 driven by CMV promoter, along with the signal peptide coding regions from various natural sources. Cells lysates and supernatant were collected then subjected to SDS-PAGE and blotted by anti-His antibody. Lane 1, GM-CSF signal peptide; Lane 2, *Gaussia* Luciferase signal peptide; Lane 3, Hidden Markov Model 38 (HMM38) signal peptide; Lane 4, antibody V gene signal peptide.

In the series of experiments described here, $2 \times 10^6$ of H293T cells transfected with either mock or plasmids contains cDNA coding His-tagged scFV-anti-PD-1 driven by CMV promoter, along with the signal peptide coding regions from various natural sources. Cells lysates and supernatant were collected 46 hours post transfection then subjected to SDS-PAGE and blotted by anti-His antibody. Forty microliter out of 2 mL of supernatant, 30 µL out of 200 µL of cell lysates were load to 12% of PAGE gel. The amounts of PD-1 scFV accumulating in supernatant of cell culture (FIG. 3) reflect efficiency of different signal peptides.

Binding Affinity of PD-1 scFV to PD-1

Figure 4:
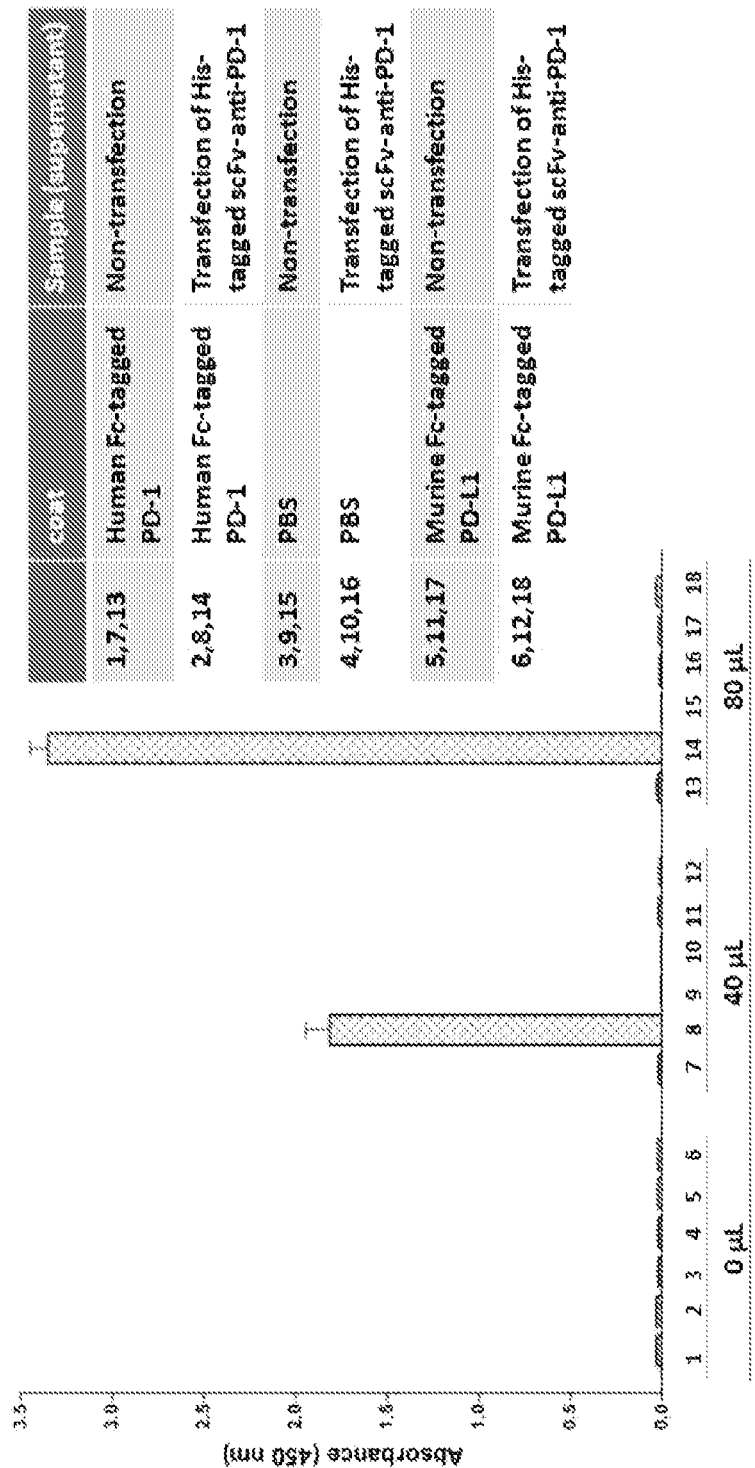
FIG. 4: Affinity assay of scFv-anti-PD-1 binding to PD-1. ELISA assay of His-tagged scFv-anti-PD-1 driven by CMV promoter, along with HMM38 signal peptide. Supernant was collected and subjected ELISA assay, detected with anti-His antibody.

$2 \times 10^6$ of H293T cells transfected with either mock or plasmids contains cDNA coding His-tagged scFV-anti-PD-1 driven by CMV promoter, along with HMM38 signal peptide. Supernatant were collected 46 hours post transfection then subjected ELISA assay, detected with anti-His antibody (FIG. 4). Secreted PD-1 scFV binds to PD-1 in a dose dependent manner.

Figure 5:
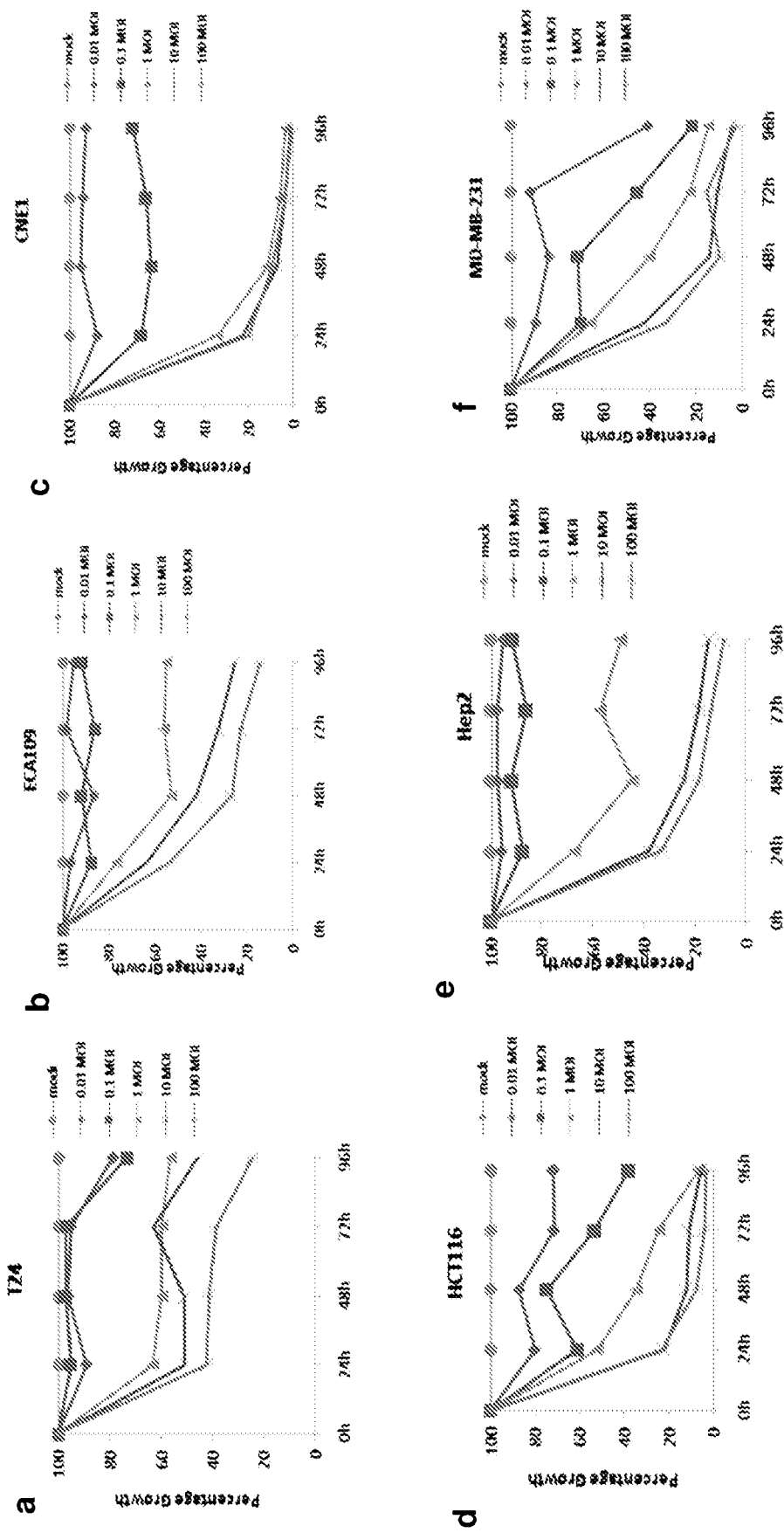
FIG. 5: in vitro cell viability of growth assay. (a): T24, human urinary bladder carcinoma; (b) ECA109, human esophageal cancer; (c) CNE1, human nasopharyngeal carcinoma; (d) HCT116, human colon carcinoma; (e) Hep2, human laryngeal carcinoma; (f) MD-MB-231, human breast cancer; (g) Hela, human epithelial adenocarcinoma; (h) A549, human lung adenocarcinoma epithelial; (i) H460, human non-small cell lung carcinoma.

In Vitro Cell Viability of Growth Assay $5\times10^3$ of human tumor cells indicated as following seeded in 96-well plates were infected either with mock (negative control) or IMMV507 (oHSV-1 expressing both PD-1 and CTLA-4 antibodies) at multiplicity of 0.01, 0.1, 1, 10 and 100 PFU per cell respectively. Cell viability of growth was measured by using CCK-8 kit every 24 hours till 96 hours (FIG. 5). The optical absorbance was determined at 450 nm by microplate Reader (BiotekEpoch).

Tumor cell lines in these studies: T24, human urinary bladder carcinoma; ECA109, human esophageal cancer; CNE1, human nasopharyngeal carcinoma; HCT116, human colon carcinoma; Hep2, human laryngeal carcinoma; MD-MB-231, human breast cancer; Hela, human epithelial adenocarcinoma; A549, human lung adenocarcinoma epithelial; H460, human non-small cell lung carcinoma.

IMMV507 killed tumor cells in a dose dependent manner. Tumor cells were reduced over time post contact with oHSV-1 viruses.

It should be understood that although the present disclosure has been specifically disclosed by preferred embodiments and optional features, modification, improvement and variation of the disclosures embodied therein herein disclosed may be resorted to by those skilled in the art, and that such modifications, improvements and variations are considered to be within the scope of this disclosure. The materials, methods, and examples provided here are representative of preferred embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein. In addition, where features or aspects of the disclosure are described in terms of Markush groups, those skilled in the art will recognize that the disclosure is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control. The disclosures illustratively described herein may suitably be practiced in the absence of any element or elements, limitation or limitations, not specifically disclosed herein. Thus, for example, the terms "comprising," "including," containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed.

LISTING OF REFERENCES

1. Andreansky, S., Soroceanu, L., Flotte, E. R., Chou, J., Markert, J. M., Gillespie, G. Y., Roizman, B., and Whitley, R. J. (1997). Evaluation of genetically engineered herpes simplex viruses as oncolytic agents for human malignant brain tumors. Cancer Res 57, 1502-1509.
2. Andreansky, S., He, B., van Cott, J., McGhee, J. V., Markert, J. M., e, Y., Roizman, B. and Whitley, R. J. Treatment of intracranial gliomas in immunocompetent mice using herpes simplex viruses that express murine interleukins. Gene Ther. 5:121-130, 1998.
3. Andtbacka, R. H., Kaufman, H. L., Collichio, F., Amatruda, T., Senzer, N., Chesney, J., Delman, K. A., Spitler, L. E., Puzanov, I., Agarwala, S. S., Milhem, M., Cranmer, L., Curti, B., Lewis, K., Ross, M., Guthrie, T., Linette, G. P., Daniels, G. A., Harrington, K., Middleton, M. R., Miller, W. H., Jr., Zager, J. S., Ye, Y., Yao, B., Li, A., Doleman, S., VanderWalde, A., Gansert, J., and Coffin, R. S. (2015). Talimogene Laherparepvec Improves Durable Response Rate in Patients With Advanced Melanoma. J Clin Oncol.
4. Brunda, M. J. (1994). Interleukin-12. J Leukoc Biol 55, 280-288.
5. Burgess, A. W., Camakaris, J., and Metcalf, D. (1977). Purification and properties of colony-stimulating factor from mouse lung-conditioned medium. J Biol Chem 252, 1998-2003.
6. Cassady, K. A., Gross, M., and Roizman, B. (1998a). The herpes simplex virus $U_S11$ protein effectively compensates for the gamma1(34.5) gene if present before activation of protein kinase R by precluding its phosphorylation and that of the alpha subunit of eukaryotic translation initiation factor 2. J Virol 72, 8620-8626.
7. Cassady, K. A., Gross, M., and Roizman, B. (1998b). The second-site mutation in the herpes simplex virus recombinants lacking the gamma134.5 genes precludes shutoff of protein synthesis by blocking the phosphorylation of eIF-2alpha. J Virol 72, 7005-7011.
8. Cheema, T. A., Wakimoto, H., Fecci, P. E., Ning, J., Kuroda, T., Jeyaretna, D. S., Martuza, R. L., and Rabkin, S. D. (2013). Multifaceted oncolytic virus therapy for glioblastoma in an immunocompetent cancer stem cell model. Proc Natl Acad Sci USA 110, 12006-12011.
9. Chou, J., Chen, J. J., Gross, M., and Roizman, B. (1995). Association of a M(r) 90,000 phosphoprotein with protein kinase PKR in cells exhibiting enhanced phosphorylation of translation initiation factor eIF-2 alpha and premature shutoff of protein synthesis after infection with gamma 134.5-mutants of herpes simplex virus 1. Proc Natl Acad Sci USA 92, 10516-10520.
10. Chou, J., Kern, E. R., Whitley, R. J., and Roizman, B. (1990). Mapping of herpes simplex virus-1 neurovirulence to gamma 134.5, a gene nonessential for growth in culture. Science 250, 1262-1266.
11. Chou, J., and Roizman, B. (1992). The gamma 1(34.5) gene of herpes simplex virus 1 precludes neuroblastoma cells from triggering total shutoff of protein synthesis characteristic of programmed cell death in neuronal cells. Proc Natl Acad Sci USA 89, 3266-3270.
12. Cozzi, P. J., Burke, P. B., Bhargav, A., Heston, W. D., Huryk, B., Scardino, P. T., and Fong, Y. (2002). Oncolytic viral gene therapy for prostate cancer using two attenuated, replication-competent, genetically engineered herpes simplex viruses. Prostate 53, 95-100.
13. Cozzi, P. J., Malhotra, S., McAuliffe, P., Kooby, D. A., Federoff, H. J., Huryk, B., Johnson, P., Scardino, P. T., Heston, W. D., and Fong, Y. (2001). Intravesical oncolytic viral therapy using attenuated, replication-competent herpes simplex viruses G207 and Nv1020 is effective in the treatment of bladder cancer in an orthotopic syngeneic model. FASEB J 15, 1306-1308.

14. Currier, M. A., Adams, L. C., Mahller, Y. Y., and Cripe, T. P. (2005). Widespread intratumoral virus distribution with fractionated injection enables local control of large human rhabdomyosarcoma xenografts by oncolytic herpes simplex viruses. Cancer Gene Ther 12, 407-416.

15. Dharmadhikari, N., Mehnert, J. M., and Kaufman, H. L. (2015). Oncolytic virus immunotherapy for melanoma. Curr Treat Options Oncol 16, 326.

16. Fife, B. T., and Pauken, K. E. (2011). The role of the PD-1 pathway in autoimmunity and peripheral tolerance. Ann N Y Acad Sci 1217, 45-59.

17. Fong, Y., Kim, T., Bhargava, A., Schwartz, L., Brown, K., Brody, L., Covey, A., Karrasch, M., Getrajdman, G., Mescheder, A., Jarnagin, W., and Kemeny, N. (2009). A herpes oncolytic virus can be delivered via the vasculature to produce biologic changes in human colorectal cancer. Mol Ther 17, 389-394.

18. Francisco, L. M., Sage, P. T., and Sharpe, A. H. (2010). The PD-1 pathway in tolerance and autoimmunity. Immunol Rev 236, 219-242.

19. Geevarghese, S. K., Geller, D. A., de Haan, H. A., Horer, M., Knoll, A. E., Mescheder, A., Nemunaitis, J., Reid, T. R., Sze, D. Y., Tanabe, K. K., and Tawfik, H. (2010). Phase I/II study of oncolytic herpes simplex virus NV1020 in patients with extensively pretreated refractory colorectal cancer metastatic to the liver. Hum Gene Ther 21, 1119-1128.

20. Goshima, F., Esaki, S., Luo, C., Kamakura, M., Kimura, H., and Nishiyama, Y. (2014). Oncolytic viral therapy with a combination of HF10, a herpes simplex virus type 1 variant and granulocyte-macrophage colony-stimulating factor for murine ovarian cancer. Int J Cancer 134, 2865-2877.

21. Hsieh, C. S., Macatonia, S. E., Tripp, C. S., Wolf, S. F., O'Garra, A., and Murphy, K. M. (1993). Development of TH1 CD4+ T cells through IL-12 produced by Listeria-induced macrophages. Science 260, 547-549.

22. Inaba, K., Inaba, M., Romani, N., Aya, H., Deguchi, M., Ikehara, S., Muramatsu, S., and Steinman, R. M. (1992). Generation of large numbers of dendritic cells from mouse bone marrow cultures supplemented with granulocyte/macrophage colony-stimulating factor. J Exp Med 176, 1693-1702.

23. Keir, M. E., Butte, M. J., Freeman, G. J., and Sharpe, A. H. (2008). PD-1 and its ligands in tolerance and immunity. Annu Rev Immunol 26, 677-704.

24. Kelly, K. J., Wong, J., and Fong, Y. (2008). Herpes simplex virus NV1020 as a novel and promising therapy for hepatic malignancy. Expert Opin Investig Drugs 17, 1105-1113.

25. Kemeny, N., Brown, K., Covey, A., Kim, T., Bhargava, A., Brody, L., Guilfoyle, B., Haag, N. P., Karrasch, M., Glasschroeder, B., Knoll, A., Getrajdman, G., Kowal, K. J., Jarnagin, W. R., and Fong, Y. (2006). Phase I, open-label, dose-escalating study of a genetically engineered herpes simplex virus, NV1020, in subjects with metastatic colorectal carcinoma to the liver. Hum Gene Ther 17, 1214-1224.

26. Krummel, M. F., and Allison, J. P. (1995). CD28 and CTLA-4 have opposing effects on the response of T cells to stimulation. J Exp Med 182, 459-465.

27. Markert, J. M., Cody, J. J., Parker, J. N., Coleman, J. M., Price, K. H., Kern, E. R., Quenelle, D. C., Lakeman, A. D., Schoeb, T. R., Palmer, C. A., Cartner, S. C., Gillespie, G. Y., and Whitley, R. J. (2012). Preclinical evaluation of a genetically engineered herpes simplex virus expressing interleukin-12. J Virol 86, 5304-5313.

28. Markert, J. M., Gillespie, G. Y., Weichselbaum, R. R., Roizman, B., and Whitley, R. J. (2000). Genetically engineered HSV in the treatment of glioma: a review. Rev Med Virol 10, 17-30.

29. Markowicz, S., and Engleman, E. G. (1990). Granulocyte-macrophage colony-stimulating factor promotes differentiation and survival of human peripheral blood dendritic cells in vitro. J Clin Invest 85, 955-961.

30. Meignier, B., Longnecker, R., and Roizman, B. (1988). In vivo behavior of genetically engineered herpes simplex viruses R7017 and R7020: construction and evaluation in rodents. J Infect Dis 158, 602-614.

31. Miest, T. S., and Cattaneo, R. (2014). New viruses for cancer therapy: meeting clinical needs. Nat Rev Microbiol 12, 23-34.

32. Mineta, T., Rabkin, S. D., Yazaki, T., Hunter, W. D., and Martuza, R. L. (1995). Attenuated multi-mutated herpes simplex virus-1 for the treatment of malignant gliomas. Nat Med 1, 938-943.

33. Russell, S. J., Peng, K. W., and Bell, J. C. (2012). Oncolytic virotherapy. Nat Biotechnol 30, 658-670.

34. Shen, Y., and Nemunaitis, J. (2006). Herpes simplex virus 1 (HSV-1) for cancer treatment. Cancer Gene Ther 13, 975-992.

35. Smith, K. D., Mezhir, J. J., Bickenbach, K., Veerapong, J., Charron, J., Posner, M. C., Roizman, B., and Weichselbaum, R. R. (2006). Activated MEK suppresses activation of PKR and enables efficient replication and in vivo oncolysis by Deltagamma(1)34.5 mutants of herpes simplex virus 1. J Virol 80, 1110-1120.

36. Topalian, S. L., Drake, C. G., and Pardoll, D. M. (2015). Immune Checkpoint Blockade: A Common Denominator Approach to Cancer Therapy. Cancer Cell 27, 450-461.

37. Valiante, N. M., Rengaraju, M., and Trinchieri, G. (1992). Role of the production of natural killer cell stimulatory factor (NKSF/IL-12) in the ability of B cell lines to stimulate T and NK cell proliferation. Cell Immunol 145, 187-198.

38. Walker, J. D., Sehgal, I., and Kousoulas, K. G. (2011). Oncolytic herpes simplex virus 1 encoding 15-prostaglandin dehydrogenase mitigates immune suppression and reduces ectopic primary and metastatic breast cancer in mice. J Virol 85, 7363-7371.

39. Walunas, T. L., Lenschow, D. J., Bakker, C. Y., Linsley, P. S., Freeman, G. J., Green, J. M., Thompson, C. B., and Bluestone, J. A. (1994). CTLA-4 can function as a negative regulator of T cell activation. Immunity 1, 405-413.

40. Weichselbaum, R. R., Roizman, B., and Whitley, R. J. (2012). Treatment of tumors with genetically engineered herpes virus. In, pp. 11-27.

41. Wong, R. J., Kim, S. H., Joe, J. K., Shah, J. P., Johnson, P. A., and Fong, Y. (2001). Effective treatment of head and neck squamous cell carcinoma by an oncolytic herpes simplex virus. J Am Coll Surg 193, 12-21.

The invention claimed is:

1. A Herpes Simplex Virus type 1 (HSV-1) vector comprising a deletion modification in a wild-type HSV-1 genome, wherein the vector comprises
   (i) sequences required for expression of all single-copy open reading frames (ORFs) in the genome, comprising the ORFs themselves and regulating sequences necessary for expression of each ORF, wherein the regulating sequences include promoters which are kept intact;
   (ii) only one copy of each of all double-copy genes in the genome; and
   (iii) only one copy of duplicated non-coding sequences in the genome.

2. The HSV-1 vector according to claim 1, wherein the double-copy genes comprise genes encoding ICP0, ICP4, ICP34.5, ORF P and ORF O.

3. The HSV-1 vector according to claim 1, wherein the HSV-1 has a genome isomer of prototype (P).

4. The HSV-1 vector according to claim 1, wherein the HSV-1 is selected from the group consisting of strains F, KOS, and 17.

5. The HSV-1 vector according to claim 4, wherein the deletion causes excision of nucleotide positions 117005 to 132096 in the genome of F strain.

6. A recombinant oncolytic Herpes Simplex Virus type 1 (HSV-1) comprising a heterologous nucleic acid sequence encoding an immunostimulatory and/or immunotherapeutic agent, that is stably incorporated into at least the deleted region of the modified HSV-1 genome of claim 1.

7. The recombinant oncolytic HSV-1 according to claim 6, wherein the immunostimulatory agent is selected from the group consisting of GM-CSF, IL 2, IL 12, IL 15, IL 24 and IL 27.

8. The recombinant oncolytic HSV-1 according to claim 6, wherein the immunotherapeutic agent is an anti-PD-1 agent or an anti-CTLA-4 agent.

9. The recombinant oncolytic HSV-1 according to claim 6, wherein the heterologous nucleic acid sequence encodes IL-12, an anti-PD-1 agent and/or an anti-CTLA-4 agent.

10. The recombinant oncolytic HSV-1 according to claim 6, wherein the heterologous nucleic acid sequence encodes IL-12 and the recombinant oncolytic HSV-1 further comprises a second heterologous nucleic acid sequence encoding an anti-PD-1 agent or an anti-CTLA-4 agent.

11. The recombinant oncolytic HSV-1 according to claim 6, wherein the heterologous nucleic acid sequence encodes an anti-PD-1 agent and the recombinant oncolytic HSV-1 further comprises a second heterologous nucleic acid sequence encoding an anti-CTLA-4 agent.

12. The recombinant oncolytic HSV-1 according to claim 6, wherein the heterologous nucleic acid sequence encodes IL-12, and the recombinant oncolytic HSV-1 further comprises a second heterologous nucleic acid sequence encoding an anti-PD-1 agent, and a third heterologous nucleic acid sequence encoding an anti-CTLA-4 agent.

13. The recombinant oncolytic HSV-1 according to claim 10, wherein the heterologous nucleic acid sequence is inserted into the deleted region of the modified HSV-1 genome, and the second heterologous nucleic acid sequence is inserted between $U_L3$ to $U_L4$ genes in the $U_L$ component of the modified HSV-1 genome.

14. The recombinant oncolytic HSV-1 according to claim 11, wherein the heterologous nucleic acid sequence is inserted into the deleted region of the modified HSV-1 genome, and the second heterologous nucleic acid sequence is inserted between $U_L3$ to $U_L4$ genes in the $U_L$ component of the modified HSV-1 genome.

15. The recombinant oncolytic HSV-1 according to claim 12, wherein the heterologous nucleic acid sequence is inserted into the deleted region of the modified HSV-1 genome, the second heterologous nucleic acid sequence is inserted between $U_L3$ to $U_L4$ genes in the $U_L$ component of the modified HSV-1 genome, and the third heterologous nucleic acid sequence is inserted between $U_L37$ to $U_L38$ genes in the $U_L$ component of the modified HSV-1 genome.

16. The recombinant oncolytic HSV-1 according to claim 12, wherein the heterologous nucleic acid sequence is inserted into the deleted region of the modified HSV-1 genome, the second heterologous nucleic acid sequence is inserted between $U_L37$ to $U_L38$ genes in the $U_L$ component of the modified HSV-1 genome, and the third heterologous nucleic acid sequence is inserted between $U_L3$ to $U_L4$ genes in the $U_L$ component of the modified HSV-1 genome.

17. A pharmaceutical composition comprising an effective amount of the recombinant oncolytic HSV-1 of claim 6 and a pharmaceutically acceptable carrier.

18. A method of treating or alleviating a cancer comprising administering to a subject in need thereof an effective amount of the pharmaceutical composition of claim 17.

19. The method according to claim 18, further comprising administering to the subject a second therapy before, at the same time, or after the pharmaceutical composition is administered.

20. The method according to claim 19, wherein the second therapy is selected from chemotherapeutic, radiotherapeutic, immunotherapeutic or surgery intervention.

21. The method according to claim 18, wherein the subject is a human being.

22. The method according to claim 18, wherein the cancer is selected from the group consisting of esophageal cancer, lung cancer, prostate cancer, and bladder cancer.

23. The HSV-1 vector of claim 1, wherein the HSV-1 vector fails to replicate in a mammal cell susceptible to the wild-type HSV-1.

24. The HSV-1 vector of claim 1, wherein the HSV-1 vector is able to replicate in a susceptible mammal cell to the wild-type HSV-1 following insertion of additional DNA sequences, wherein the additional DNA sequences are cellular or viral DNA sequences.

25. The HSV-1 vector of claim 1, wherein the deletion causes one copy of duplicated non-coding sequences including introns of ICP0, LAT domain and "a" sequence deleted.

26. A Herpes Simplex Virus type 1 (HSV-1) vector comprising a deletion modification in a wild-type HSV-1 genome, wherein the HSV-1 vector fails to replicate in a mammal cell susceptible to the wild-type HSV-1 but becomes able to replicate following insertion of additional DNA sequences.

27. The HSV-1 vector of claim 1, wherein the deletion modification comprises a deletion starting from the promoter of the last gene in the $U_L$ component to the first gene in the $U_S$ component in case of an $I_L$ isomer of HSV-1 genome.

28. The HSV-1 vector of claim 27, wherein the last known gene in the $U_L$ component is $U_L1$ in case of the $I_L$ isomer.

29. The HSV-1 vector of claim 27, wherein the first known gene in the $U_S$ component is $U_S1$ in case of the $I_L$ isomer.

* * * * *